(12) United States Patent
Weiner et al.

(10) Patent No.: US 9,113,968 B2
(45) Date of Patent: Aug. 25, 2015

(54) DYNAMIC BONE PLATE COMPRESSION DEVICE AND METHOD

(71) Applicant: Nextremity Solutions, Inc., Red Bank, NJ (US)

(72) Inventors: Lon S. Weiner, Rumson, NJ (US); Stuart D. Katchis, Scarsdale, NY (US); John R. Pepper, Cheshire, CT (US)

(73) Assignee: Nextremity Solutions, Inc., Red Bank, NJ (US)

( * ) Notice: Subject to any disclaimer, the term of this patent is extended or adjusted under 35 U.S.C. 154(b) by 163 days.

(21) Appl. No.: 13/752,334

(22) Filed: Jan. 28, 2013

(65) Prior Publication Data
US 2014/0214036 A1 Jul. 31, 2014

(51) Int. Cl.
*A61B 17/56* (2006.01)
*A61B 17/58* (2006.01)
*A61B 17/80* (2006.01)
*A61F 2/00* (2006.01)

(52) U.S. Cl.
CPC .......... *A61B 17/8004* (2013.01); *A61B 17/808* (2013.01); *A61B 17/8009* (2013.01); *A61B 17/8019* (2013.01); *A61B 17/8023* (2013.01)

(58) Field of Classification Search
CPC .......... A61B 17/8004; A61B 17/8009; A61B 17/808; A61B 17/8023; A61B 17/8019
USPC .......................... 606/280, 281, 282, 286, 291
See application file for complete search history.

(56) References Cited

U.S. PATENT DOCUMENTS

| | | | |
|---|---|---|---|
| 5,628,740 A * | 5/1997 | Mullane | 606/307 |
| 2005/0010218 A1 | 1/2005 | Dalton | |
| 2006/0100625 A1 | 5/2006 | Ralph | |

(Continued)

FOREIGN PATENT DOCUMENTS

| | | |
|---|---|---|
| DE | 20 2007 001585 U1 | 5/2007 |
| FR | 2796829 A1 | 2/2001 |

(Continued)

OTHER PUBLICATIONS

European Search Report for corresponding European Application 14152883.6, mailed on May 14, 2014.

*Primary Examiner* — Christopher Beccia
*Assistant Examiner* — Diana S Jones
(74) *Attorney, Agent, or Firm* — Heslin Rothenberg Farley & Mesiti P.C.

(57) ABSTRACT

A dynamic bone plate and method of bone compression is disclosed. The dynamic bone plate comprises a first bone plate component and a second bone plate component. The first bone plate component comprises at least one hole configured for receiving bone screws for attachment to a first bone segment; and a male component. The second bone plate component comprises at least one hole configured for receiving bone screws for attachment to a second bone segment; and a female component configured for mating with the male component of the first bone plate component. The male component is adjustable after mating with the female component to adjust a position of the first bone plate component with respect to the second bone plate component and wherein the male component is locked into place with respect to the female component by at least one bone screw inserted through the at least one hole of the second bone plate component causing compression between the first bone segment and the second bone segment to form a corrective construct.

21 Claims, 36 Drawing Sheets

(56) References Cited

U.S. PATENT DOCUMENTS

2007/0173841 A1* 7/2007 Ralph et al. ............... 606/69
2012/0265203 A1* 10/2012 Angelucci et al. ......... 606/70

FOREIGN PATENT DOCUMENTS

WO 03000148 A2 1/2003
WO 2008051967 A3 5/2008

* cited by examiner

DYNAMIC BONE PLATE COMPRESSION DEVICE AND METHOD

TECHNICAL FIELD

The present disclosure relates to corrective surgery and bone fixation.

BACKGROUND OF THE INVENTION

Numerous devices have been implemented for joining bone pieces. For example, see, e.g., U.S. Pat. No. 3,866,607; U.S. Patent Publications 2005/0043732, 2006/0036240, 2007/0123880, 2007/0270855, 2007/0293863, 2008/0147124, 2009/0234359, and 2009/0192514; and PCT Patent Publications WO 2007/12622 and WO 2009/062522. However, the devices described by the aforementioned publications do not allow for precise fine tuning adjustments to be made. More specifically, the devices do not allow specific adjustments to be made to the amount of compression applied to bone pieces, which renders these devices difficult to use for more complicated procedures such as certain fracture repairs and bone fusions that require precision.

SUMMARY OF THE INVENTION

A method and system for bone fixation is disclosed. More specifically, a method and system for corrective surgery by bone compression is disclosed.

In an embodiment, a dynamic bone plate is disclosed. The dynamic bone plate comprises a first bone plate component and a second bone plate component. The first bone plate component comprises at least one hole configured for receiving bone screws for attachment to a first bone segment; and a male component. The second bone plate component comprises at least one hole configured for receiving bone screws for attachment to a second bone segment; and a female component configured for mating with the male component of the first bone plate component. The male component is adjustable after mating with the female component to adjust a position of the first bone plate component with respect to the second bone plate component and wherein the male component is locked into place with respect to the female component by at least one bone screw inserted through the at least one hole of the second bone plate component causing compression between the first bone segment and the second bone segment to form a corrective construct.

In another embodiment, the male component comprises an elongated member receivable by the female component in a dovetail configuration.

In another embodiment, the female component comprises a dovetail receptacle configured for receiving the male component in a dovetail configuration.

In another embodiment, the male component and the female component, when mated, fit telescopically.

In another embodiment, tightening of a bone screw inserted through a hole of the at least one hole of the second bone plate component, causes a head of the bone screw to impinge on the male component mated with the female component and lock the male component in place within the female component.

In another embodiment, tightening of a secondary locking bone screw inserted through a hole of the at least one hole of the second bone plate component, causes the male component to lock into place within the female component by interference. When the secondary locking bone screw is not fully screwed through the hole, the male component is capable of sliding within the female component.

In another embodiment, the male component comprises teeth for engaging with the female component, wherein the teeth function as a gear rack.

In another embodiment, the female component comprises serrations to increase resistance with respect to movement of the male component within the female component.

In another embodiment, the second plate component comprises a plurality of female components, each female component configured for mating with a corresponding male component.

In another embodiment, the first plate component comprises a base component comprising the at least one hole configured for receiving bone screws for attachment to a first bone segment, and a multiplanar component comprising the male component; and at least one hole configured for receiving bone screws. The base component may further comprise a spherical concave section configured for receiving the multiplanar component, facilitating a ball joint type motion between the spherical concave section and the multiplanar component. The multiplanar component may be locked down into the base component with at least one bone screw which may be inserted through both at least one hole of the multiplanar component and at least one hole of the base component. The spherical concave section may allow the male component to be placed at varying angles in the base component with respect to the base component.

In another embodiment, the second plate component further comprises a ratcheting pawl. The ratcheting pawl may restrict the movement of the male component within the female component. The ratcheting pawl may be locked into place by a bone screw inserted and tightened through a hole of the second plate component.

In another embodiment, the bone screws each comprise at least one thread.

In another embodiment, the bone screws are each dual thread screws. The dual thread screws may each comprise a bone thread and a machine thread, the bone thread configured for attaching to bone, and the machine thread configured for attaching to portions of the dynamic bone plate.

In another embodiment, the multiplanar component is preformed.

In another embodiment, the bone screws are screwed through the at least one holes using an external tool. The external tool may comprise at least two pins.

In another embodiment, the male component snaps into the female component.

In another embodiment, the first bone plate component comprises a recessed hole configured to receive a bone screw that holds both the first bone plate component and the second bone plate component together after the male component has mated with the female component.

In an embodiment, a dynamic plate Is disclosed. The dynamic plate comprises a first plate component and a second plate component. The first plate component comprises at least one hole configured for receiving screws for attachment to a first body segment; and a male component. The second plate component comprises at least one hole configured for receiving screws for attachment to a second body segment; and a female component configured for mating with the male component of the first plate component. The male component is adjustable after mating with the female component to adjust a position of the first plate component with respect to the second plate component and wherein the male component is locked into place with respect to the female component by at least one screw inserted through the at least one hole of the second plate component causing compression between the first body segment and the second body segment to form a corrective construct.

In another embodiment, the male component comprises an elongated member receivable by the female component in a dovetail configuration.

In another embodiment, the female component comprises a dovetail receptacle configured for receiving the male component in a dovetail configuration.

In another embodiment, the male component and the female component, when mated, fit telescopically.

In another embodiment, tightening of a screw inserted through a hole of the at least one hole of the second plate component, causes a head of the screw to impinge on the male component mated with the female component and lock the male component in place within the female component.

In another embodiment, tightening of a secondary locking screw inserted through a hole of the at least one hole of the second plate component, causes the male component to lock into place within the female component by interference. When the secondary locking bone screw is not fully screwed through the hole, the male component is capable of sliding within the female component.

In another embodiment, the male component comprises teeth for engaging with the female component, wherein the teeth function as a gear rack.

In another embodiment, the female component comprises serrations to increase resistance with respect to movement of the male component within the female component.

In another embodiment, the second plate component comprises a plurality of female components, each female component configured for mating with a corresponding male component.

In another embodiment, the first plate component comprises a base component comprising the at least one hole configured for receiving screws for attachment to a first body segment; and a multiplanar component comprising the male component; and at least one hole configured for receiving screws. The base component further comprises a spherical concave section configured for receiving the multiplanar component, facilitating a ball joint type motion between the spherical concave section and the multiplanar component. The multiplanar component may be locked down into the base component with at least one screw which may be inserted through both at least one hole of the multiplanar component and at least one hole of the base component. The spherical concave section may allow the male component to be placed at varying angles in the base component with respect to the base component.

In another embodiment, the second plate component further comprises a ratcheting pawl. The ratcheting pawl may restrict movement of the male component within the female component. The ratcheting pawl may be locked into place by a screw inserted and tightened through a hole of the second plate component.

In another embodiment, the screws each comprise at least one thread

In another embodiment, the screws are each dual thread screws. The multiplanar component may be preformed.

In another embodiment, the screws are screwed through the at least one holes using an external tool. The external tool may comprise at least two pins.

In another embodiment, the male component snaps into the female component.

In another embodiment, the first plate component comprises a recessed hole configured to receive a screw that holds both the first plate component and the second plate component together after the male component has mated with the female component.

In an embodiment, a method for bone compression is disclosed. A bone plate is placed over a bone comprising a first bone segment and a second bone segment. A first bone plate component of the bone plate is attached to the first bone segment. A second bone plate component of the bone plate is attached to the second bone segment. The male component of the first bone plate component is mated with a female component of the second bone plate component. A position of the male component is adjusted with respect to the female component to cause an adjustment of position of the first bone plate component with respect to the second bone plate component. The first bone plate component is locked to the second bone plate component to cause compression between the first bone segment and the second bone segment to form a corrective construct.

These and other advantages of the embodiments of the present disclosure will be apparent to those of ordinary skill in the art by reference to the following Detailed Description and accompanying drawings/figures.

DETAILED DESCRIPTION

A method and system for bone fixation is disclosed herein. More specifically, a method and system for corrective surgery by bone compression is disclosed. The present disclosure provides disclosure of a plate that facilitates the compression of bone segments or bone pieces. The concepts described herein in relation to bone plates may also be applicable to other body parts such as joints. The present disclosure describes bone plates comprising at least two components that mate with each other to form a corrective construct from two bone segments.

Provided herein is a device and method for carrying out corrective surgery and bone fixation. In the various embodiments described herein and corresponding with the Figures provided herewith, a bone plate is disclosed. The bone plate may be a compression bone plate which is dynamic and facilitates fine adjustments to provide precision during bone correction procedures. In an embodiment, the bone plate comprises a first bone plate component and a second bone plate component. The first bone plate component may comprise at least one hole configured for receiving bone screws for attachment to a first bone segment, and a male component. The second bone plate component may comprise at least one hole configured for receiving bone screws for attachment to a second bone segment, and a female component configured for mating with the male component of the first bone plate component. The male component is adjustable after mating with the female component to adjust a position of the first bone plate component with respect to the second bone plate component. The male component may be locked into place with respect to the female component by at least one bone screw inserted through at least one hole of the second bone plate component.

Figure 1:
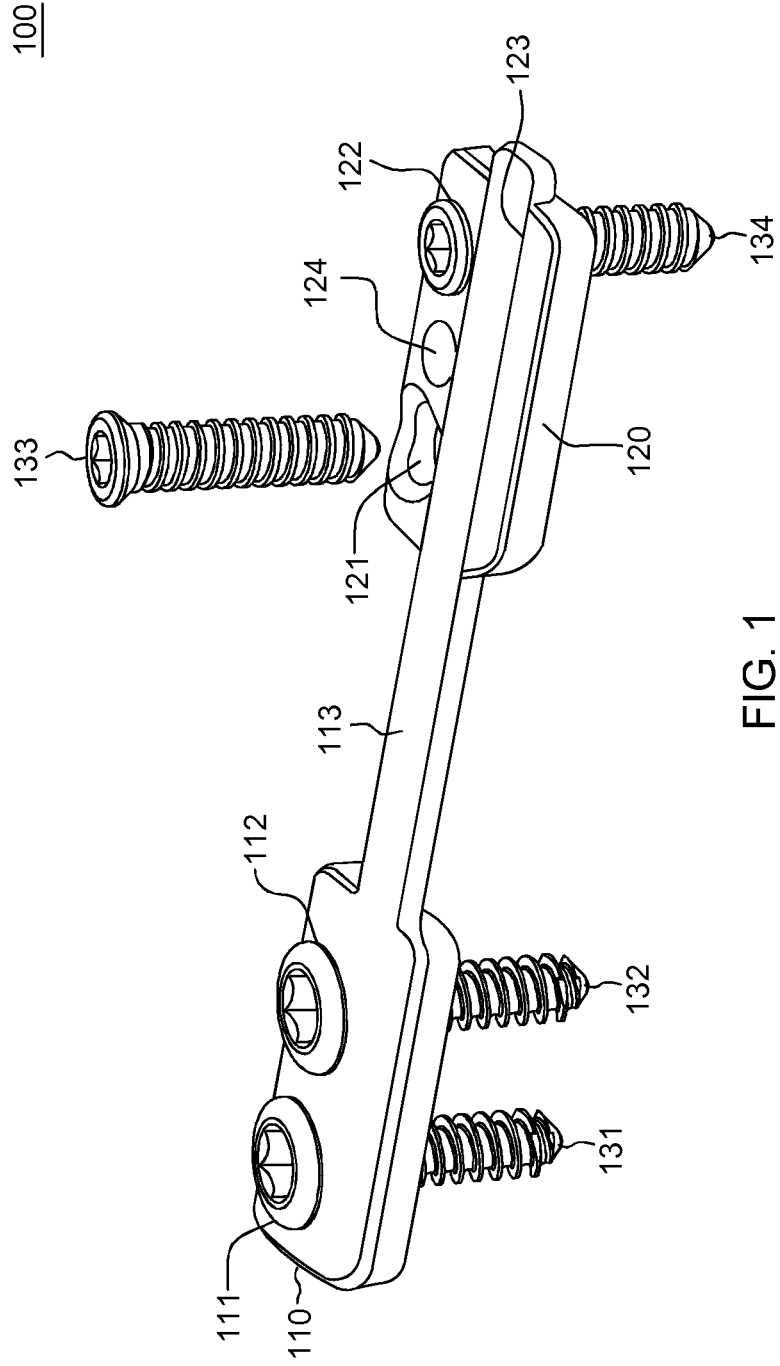
FIG. 1 illustrates an exemplary bone plate in a dovetail implementation, in accordance with an embodiment.

FIG. 1 illustrates an exemplary bone plate in a dovetail implementation, in accordance with an embodiment. FIG. 1 illustrates a dovetail implementation of a bone plate in accordance with an embodiment of the present disclosure. Bone plate 100, as shown, includes a first bone plate component 110 and a second bone plate component 120. First bone plate component 110 includes holes 111 and 112 for receiving bone screws 131 and 132, respectively. Bone screws 131 and 132 are screwed into a first bone segment (not shown) through holes 111 and 112, respectively, to attach first bone plate component 110 to the first bone segment. First bone plate component 110 also includes a male component 113 or dovetail, which is used for attaching first bone plate component 110 to second bone plate component 120 to facilitate compression of each of first bone plate component 110 and second bone plate component 120, which causes compression between the first bone segment and a second bone segment attached to second bone plate component 120. The compression results in the creation of a corrective bone construct. Second bone plate component 120 also includes holes, such as holes 121 and 122, for receiving screws 133 and 134, respectively. Bone screws 133 and 134 are screwed into a second bone segment (not shown) through holes 121 and 122, respectively, to attach second bone plate component 120 to the second bone segment. Second bone plate component 120 also includes a female component 123, which may comprise a receptacle for receiving male component 113. Male component 113 and female component 123 are slidably coupled and fit together telescopically.

After male component 113 has been inserted into or mated with female component 123, the position of male component 113 within female component 123 is adjustable, which results in an adjustment of the position of first bone plate component 110 with respect to second bone plate component 120. As each of first bone plate component 110 and second bone plate component 120 are attached to a corresponding bone segment, the position of the bone segments are also thus adjustable. Adjustment may result in compression of the bone segments, causing the bone segments to move closer to each other to form a corrective construct.

After adjustment of male component 113 within female component 123 is complete, the first bone plate component 110 and the second bone plate component 120 must be locked into place. Locking may be facilitated by numerous means. In an embodiment, a bone screw, such as those shown, may be tightened, resulting in the head of the bone screw impinging on the male component 113, which results in locking the male component 113 in place. In another embodiment, a secondary locking screw, when tightened, may lock male component 113 in place by interference. Thus, when the screw is not fully seated or fully screwed into a screw hole, male component 113 may move freely, and thus be adjustable, until the screw is fully tightened.

For example, hole 124, may be used as a dedicated hole for receiving a bone screw or locking screw which locks male component 113 in place based on at least the locking methods described above. Alternatively, male component 113 may be notched and the screw inserted into hole 124 may be inserted into and secured with the notch of male component 113.

While the embodiments described herein each embody different characteristics, it is understood to one of ordinary skill in the art that features of all embodiments described herein with respect to each of the individual Figures may be combined with features described with respect to other Figures of the present disclosure.

Figure 2:
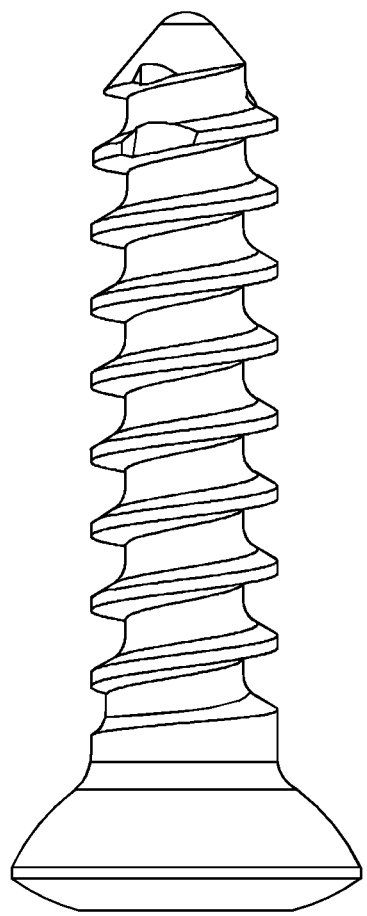
FIG. 2 illustrates a view of a bone screw, in accordance with an embodiment.

FIG. 2 illustrates a view of a bone screw, in accordance with an embodiment. FIG. 2 illustrates a conventional bone screw that may be used to affix bone plates to bone segments or body segments, in accordance with the embodiments described herein.

Figure 3:
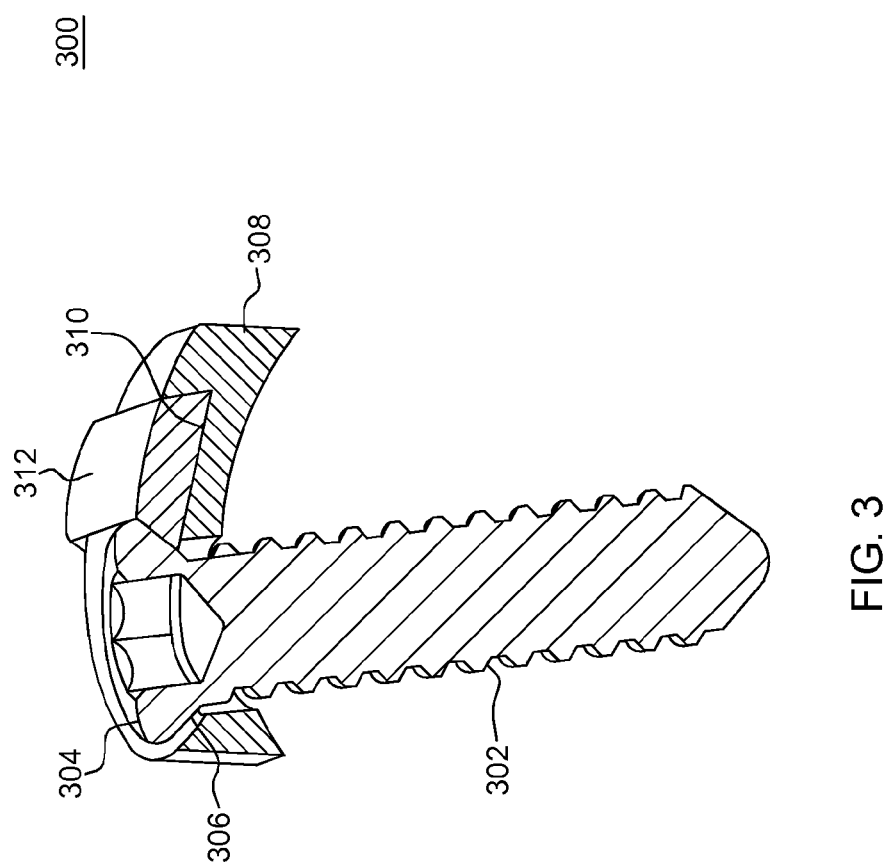
FIG. 3 illustrates a cross section view of how a bone screw contacts an angular surface of a bone plate, in accordance with an embodiment.

FIG. 3 illustrates a cross section view of how a bone screw contacts an angular surface of a bone plate, in accordance with an embodiment. FIG. 3 illustrates how a top portion of a bone screw may lock a male component into place within a female component. For example, bone screw 302 as shown, includes a bone screw top 304. Bone screw 302 has been inserted through hole 306 of a second plate component 308. Second plate component 308 includes a female component 310 which may be a receptacle for receiving a male component 312. Bone screw top 304, as shown, contacts an angular surface of male component 312. As bone screw 302 is screwed tighter within hole 306, bone screw top 304 increases contact and impinges the angular surface of male component 312 which is nestled within female component 310. This locks male component 312 into place within female component 310 and thus locks a first plate component and second plate component in position with respect to each other and as a result, locks the position of a first and second bone segment to form a corrective construct.

Figure 4A:
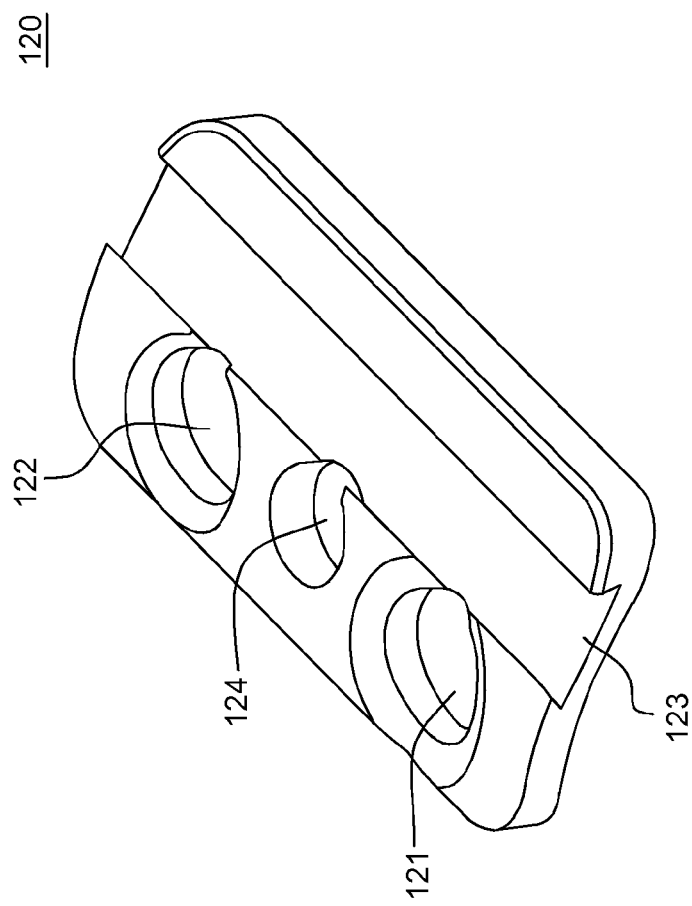
FIG. 4A illustrates a perspective view of a component of a bone plate, in accordance with an embodiment.

FIG. 4A illustrates a perspective view of a component of a bone plate, in accordance with an embodiment. FIG. 4A shows a perspective view of second bone plate component 120, including female component 123, and holes 121, 122, and 124. The perspective view shows how each of the holes 121, 122, and 124 facilitate locking of a male component inserted into female component 123 when a bone screw is inserted and tightened into each of the holes.

Figure 4B:
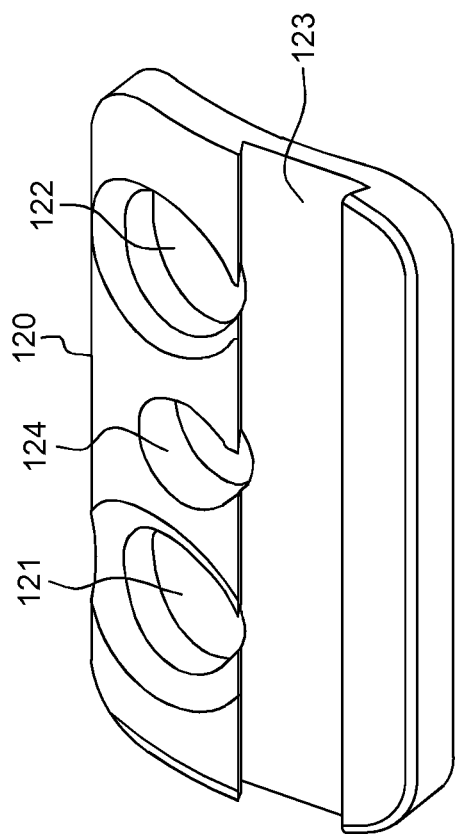
FIG. 4B illustrates another perspective view of a component of a bone plate, in accordance with an embodiment.

4B illustrates another perspective view of a component of a bone plate, in accordance with an embodiment. FIG. 4B shows a different perspective of the second bone plate component 120 as also shown by 4A.

Figure 5:
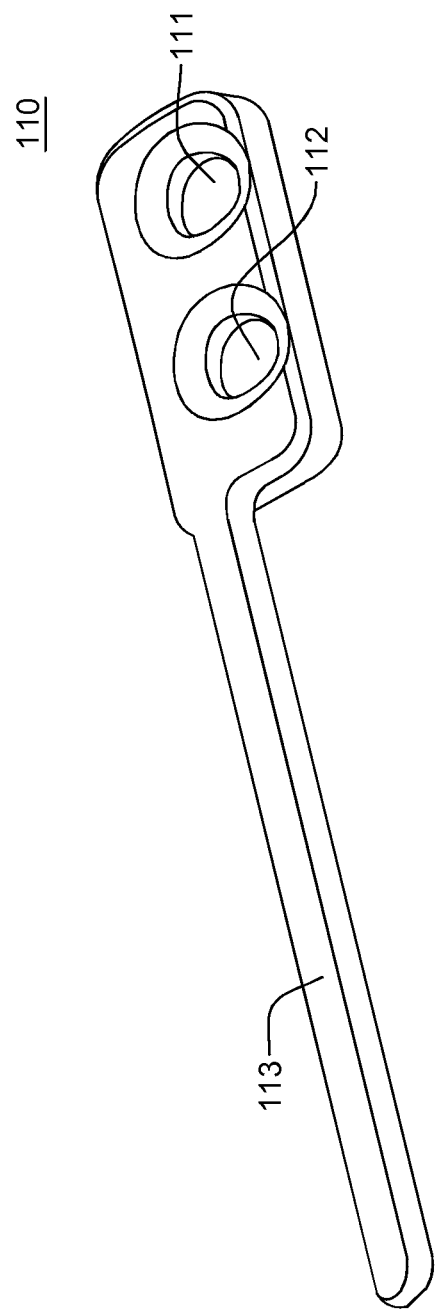
FIG. 5 illustrates a perspective view of a component of a bone plate, in accordance with an embodiment.

FIG. 5 illustrates a perspective view of a component of a bone plate, in accordance with an embodiment. FIG. 5 shows a perspective view of first bone plate component 110. Holes 111 and 112 are shown for receiving bone screws. Male component 113 is also shown, wherein male component 113 is configured for mating with female component of second bone plate component 120 as shown by FIG. 4A and 4B, as well as FIG. 1.

Figure 6:
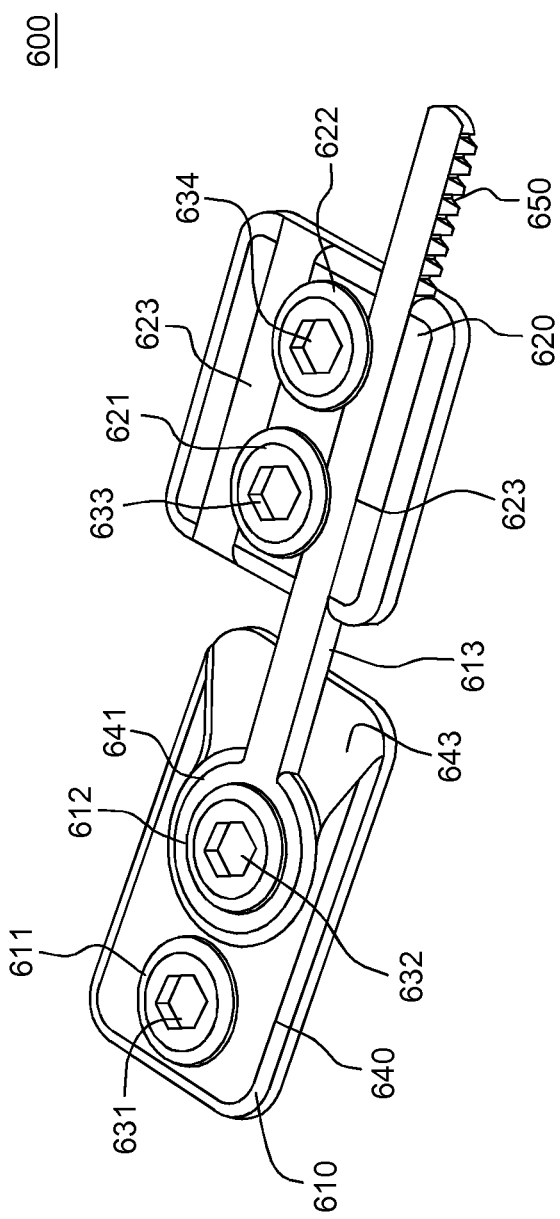
FIG. 6 illustrates an exemplary bone plate in an alternate dovetail implementation, in accordance with an embodiment.

FIG. 6 illustrates an exemplary bone plate in an alternate dovetail implementation, in accordance with an embodiment. Bone plate 600, as shown, includes a first bone plate component 610 and a second bone plate component 620. First bone plate component 610 may include a base component 640 which includes holes 611 and 612 for receiving bone screws 631 and 632, respectively. Bone screws 631 and 632 are screwed into a first bone segment (not shown) through holes 611 and 612, respectively, to attach first bone plate component 610 to the first bone segment. First bone plate component 610 also includes a male component 613 which is used for attaching first bone plate component 610 to second bone plate component 620 to facilitate compression of each of first bone plate component 610 and second bone plate component 620, which causes compression between the first bone segment and a second bone segment attached to second bone plate component 620. Male component 613 may include a hole 641 for receiving bone screw 632 that goes through both hole 641 and hole 612 to hold and/or lock male component 613 to base component 640 of first bone plate component 610. Base component 640 further includes a bearing surface 643 which facilitates multiplanar movement of male component 613, allowing for angular adjustments to be made to male component 613. The compression results in the creation of a corrective bone construct. A spherical bearing surface as shown may facilitate reduction of complex fractures or closure of segments as opposed to those without geometric surfaces or pathways.

In an embodiment, male component 613 is placed into the bearing surface 643 of base component 640. Once a multiplanar angle of male component 613 has been selected, a bone screw 632 may be inserted through both hole 612 and hole 641. Once bone screw 632 is tightened or fastened, male component 613 is locked into place in bearing surface 643 with respect to base component 640.

Second bone plate component 620 also includes holes, such as holes 621 and 622, for receiving screws 633 and 634, respectively. Bone screws 633 and 634 are screwed into a second bone segment (not shown) through holes 621 and 622, respectively, to attach second bone plate component 620 to the second bone segment. Second bone plate component 620 also includes at least one female component 623, which may comprise a receptacle for receiving a male component such as male component 613.

Either or both male component 613 or any of female components 623 may include serrations or grooves to increase resistance, thus providing a more secure locking mechanism and also allowing for more precise adjustments. For example, male component 613 includes teeth or serrations 650 cut along a portion of its bottom surface. This allows male component 613 to function as a gear rack. Thus, an external pinion gear (not shown) may engage the teeth or serrations to provide bone compression, distraction, or both. Turning or usage of the pinion gear will cause adjustment of a position of the male component 613 in either of two directions laterally with respect to female component 623. This in turn results in adjustments of position between first bone plate component 610 and second bone plate component 620.

Second bone plate component 620 as shown includes two female components 623. Usage of multiple female components facilitates connection with multiple male components to further provide stability in joining bone or body segments using bone plate 600.

In an embodiment, male component 613 is locked into place within female component 623 based on a tightening of bone screws 633 and 634. As shown in FIG. 6, bone screws 633 and 634, when tightened, press against male component 613, thereby preventing male component 613 from moving within female component 623.

Figure 7:
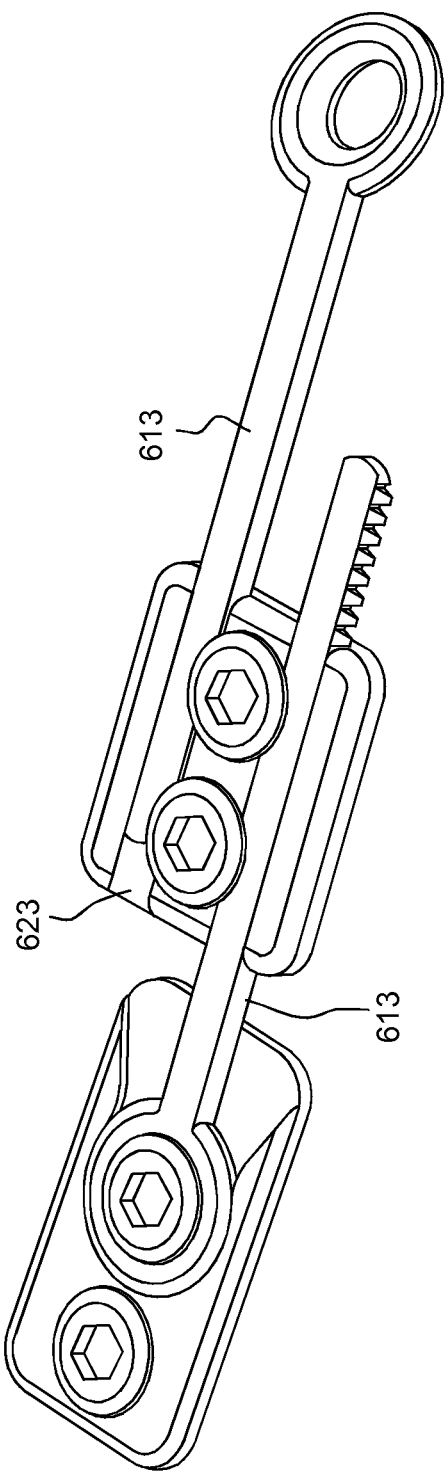
FIG. 7 illustrates an exemplary bone plate in an alternate dovetail implementation, in accordance with an embodiment.

FIG. 7 illustrates an exemplary bone plate in an alternate dovetail implementation, in accordance with an embodiment. FIG. 7 illustrates bone plate 600 as also shown by FIG. 6. Bone plate 600 as shown additionally includes a second male component 613 mated with female component 623. The addition of another male component provides further stability for forming a corrective construct and also facilitates the addition of another base component 640 in conjunction with the second male component 613.

Figure 8:
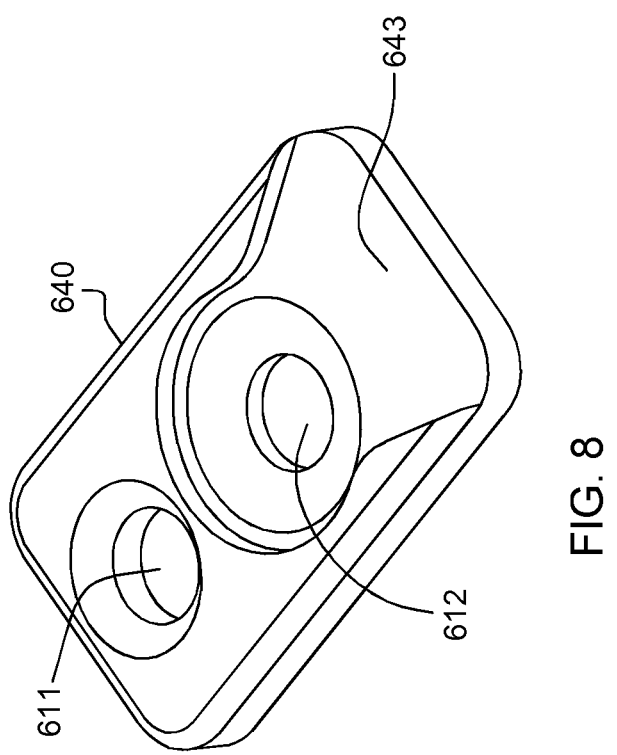
FIG. 8 illustrates an exemplary plate component, in accordance with an embodiment.

FIG. 8 illustrates an exemplary plate component, in accordance with an embodiment. FIG. 8 provides a close up view of base component 640 of first bone plate component 610. As shown, base component 640 includes holes 611 and 612. These holes facilitate insertion of bone screws to attach base component 640 to a first bone segment. Also shown is spherical bearing surface 643, which may be concave, and facilitates a ball joint type motion to occur when a male component is placed therein. Once a male component is placed within spherical bearing surface 643, a bone screw, or a screw with machine threads may be used to lock down the male component within bearing surface 643. As bearing surface 643 is concave and allows multiplanar motion, prior to locking down the male component, the male component may be adjusted at a desired angle.

Figure 9:
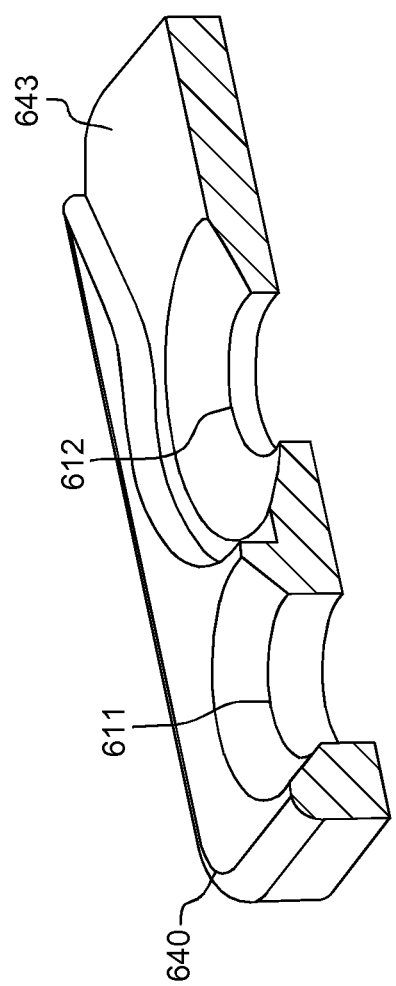
FIG. 9 illustrates a sectional view of an exemplary plate component, in accordance with an embodiment.

FIG. 9 illustrates a sectional view of an exemplary plate component, in accordance with an embodiment. FIG. 9 shows a sectional view of base component 640 to more clearly show holes 611 and 612, as well as a different perspective view of spherical bearing surface 643 which receives a male component which is locked by insertion of a bone screw or other type of screw through hole 612.

Figure 10:
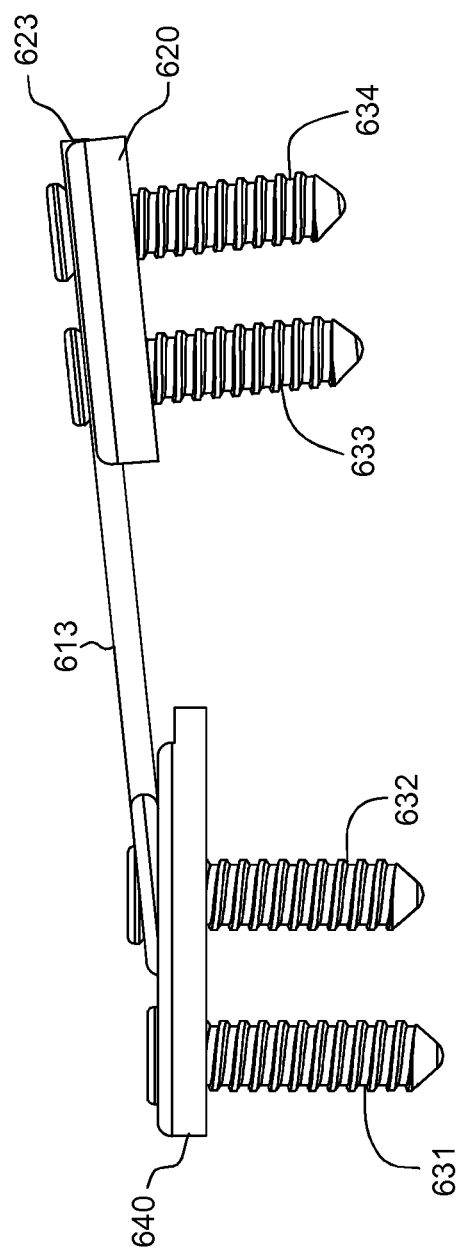
FIG. 10 illustrates a side view of an exemplary bone plate, in accordance with an embodiment.

FIG. 10 illustrates a side view of an exemplary bone plate, in accordance with an embodiment. FIG. 10 illustrates a side view of bone plate 600 after it has been completely affixed to a first and second bone segment (not shown) using bone screws 631, 632, 633, and 634. A side perspective view allows a view of an exemplary positioning of male component 613, which is positioned at an acute angle with respect to base component 640. Male component 613 is locked down into base component 640 by bone screw 632. Male component 613 is also mated with female component 623 and is locked into place within female component 623 by bone screws 633 and 634.

Figure 11:
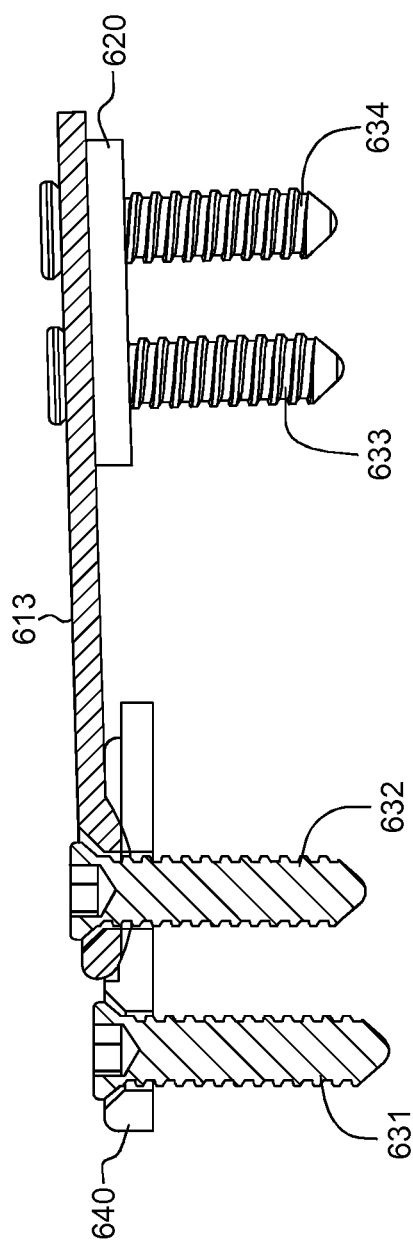
FIG. 11 illustrates a sectional view of an exemplary bone plate, in accordance with an embodiment.

FIG. 11 illustrates a sectional view of an exemplary bone plate, in accordance with an embodiment. FIG. 11 illustrates a sectional view of bone plate 600 after it has been completely affixed to a first and second bone segment (not shown) using bone screws 631, 632, 633, and 634. A sectional view allows a view of an exemplary positioning of male component 613 at an angle within the same plane as base component 640. Male component 613 is locked down into base component 640 by bone screw 632. Male component 613 is also mated with female component 623 and is locked into place within female component 623 by bone screws 633 and 634.

Figure 12:
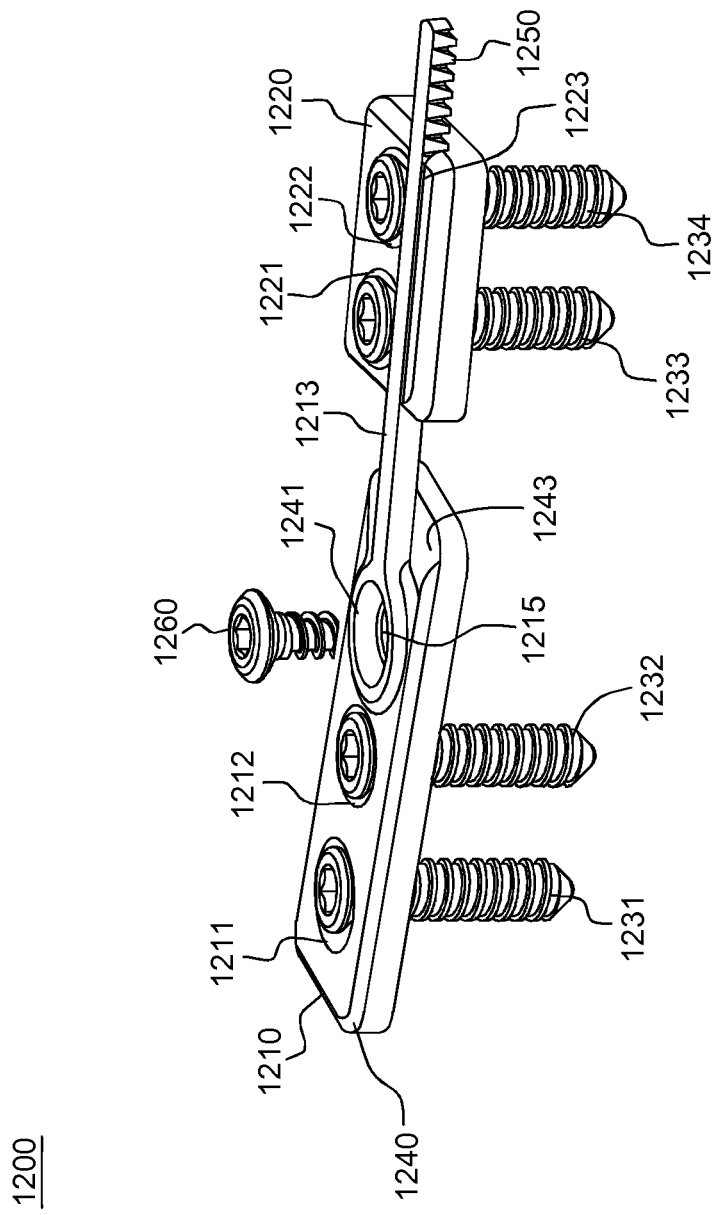
FIG. 12 illustrates an exemplary bone plate including a discrete locking screw construct, in accordance with an embodiment.

FIG. 12 illustrates an exemplary bone plate including a discrete locking screw construct, in accordance with an embodiment. Bone plate 1200 as shown by FIG. 12 facilitates locking of a male component 1213 to a base component 1240 of a first bone plate component 1210 by using a discrete locking screw construct comprising a machine threaded dedicated screw 1241 that may be inserted through hole 1241 of male component 1213 and through hole 1215 of base component 1240.

Bone plate 1200, as shown, includes a first bone plate component 1210 and a second bone plate component 1220. First bone plate component 1210 may include a base component 1240 which includes holes 1211 and 1212 for receiving bone screws 1231 and 1232, respectively. Base component 1240 also includes hole 1215 for receiving screw 1260 as discussed above. Bone screws 1231 and 1232 are screwed into a first bone segment (not shown) through holes 1211 and 1212, respectively, to attach first bone plate component 1210 to the first bone segment. Screw 1260 is used to fasten male component 1613 to base component 1640.

First bone plate component 1210 also includes a male component 1213 which is used for attaching first bone plate component 1210 to second bone plate component 1220 to facilitate compression of each of first bone plate component 1210 and second bone plate component 1220, which causes compression between the first bone segment and a second bone segment attached to second bone plate component 1220. Male component 1213, as discussed above, may include a hole 1241 for receiving screw 1260 which may comprise machine threads. that goes through both hole 1241 and hole 1215 to hold and/or lock male component 1213 to base component 1240 of first bone plate component 1210. Base component 1240 further includes a bearing surface 1243 which facilitates multiplanar movement of male component 1213, allowing for angular adjustments to be made to male component 1213. The compression results in the creation of a corrective bone construct. A spherical bearing surface facilitates reduction of complex fractures or closure of segments without geometric surfaces or pathways.

In an embodiment, male component 1213 is placed into the bearing surface 1243 of base component 1240. Once a multiplanar angle of male component 1213 has been selected, a screw 1260 may be inserted through both hole 1215 and hole 1241. Once screw 1260 is tightened or fastened, male component 1213 is locked into place in bearing surface 1243 with respect to base component 1240.

Second bone plate component 1220 also includes holes, such as holes 1221 and 1222, for receiving screws 1233 and 1234, respectively. Bone screws 1233 and 1234 are screwed into a second bone segment (not shown) through holes 1221 and 1222, respectively, to attach second bone plate component 1220 to the second bone segment. Second bone plate component 1220 also includes a female component 1223, which may comprise a receptacle for receiving a male component such as male component 1213.

Either or both male component 1213 and female components 1223 may include serrations or grooves to increase resistance, thus providing a more secure locking mechanism and also allowing for more precise adjustments. For example, male component 1213 includes teeth or serrations 1250 cut along a portion of its bottom surface. This allows male component 1213 to function as a gear rack. Thus, an external pinion gear (not shown) may engage the teeth or serrations to provide bone compression, distraction, or both. Turning or usage of the pinion gear will cause adjustment of a position of the male component 1213 in either of two directions laterally with respect to female component 1223. This in turn results in adjustments of position between first bone plate component 1210 and second bone plate component 1220. alternatively, the teeth may be in the side of the male component 1213.

In an embodiment, male component 1213 is locked into place within female component 1223 based on a tightening of bone screws 1233 and 1234. As shown in FIG. 12, bone screws 1233 and 1234, when tightened, press against male component 1213, thereby preventing male component 1213 from moving within female component 1223.

Figure 13:
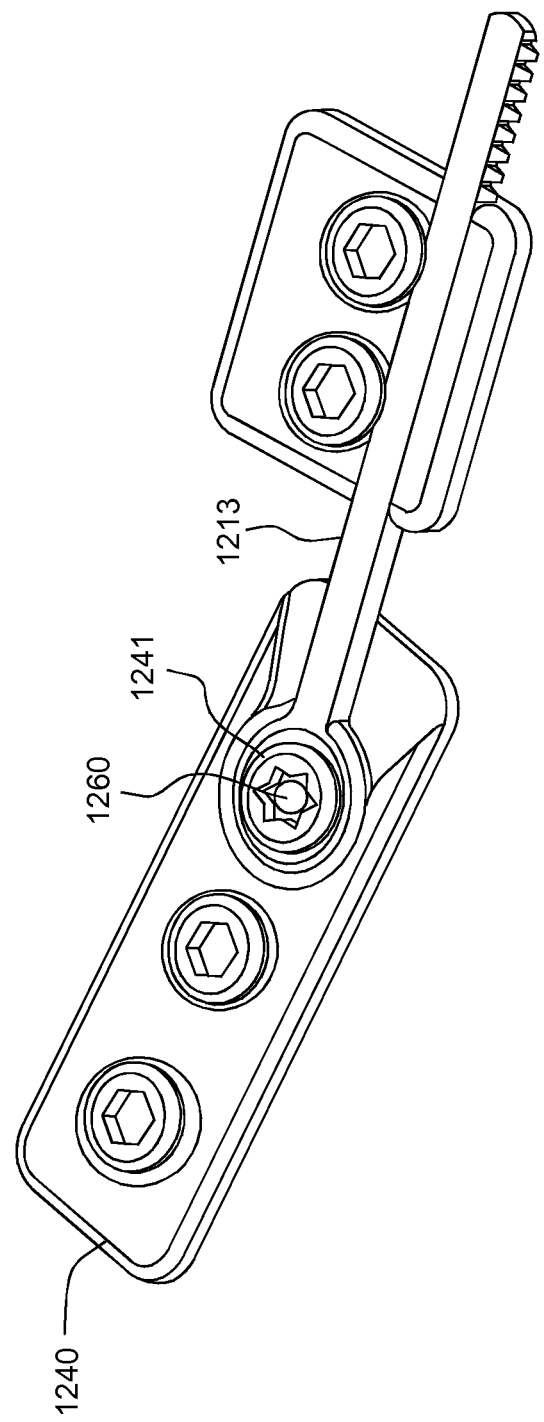
FIG. 13 illustrates an exemplary bone plate including a discrete locking screw construct, in accordance with an embodiment.

FIG. 13 illustrates an exemplary bone plate including a discrete locking screw construct, in accordance with an embodiment. FIG. 13 illustrates a top perspective view of bone plate 1200 as also shown in FIG. 12. Screw 1260 as shown is fully inserted through holes 1241 and 1215 to lock male component 1213 in place with respect to base component 1240.

Figure 14:
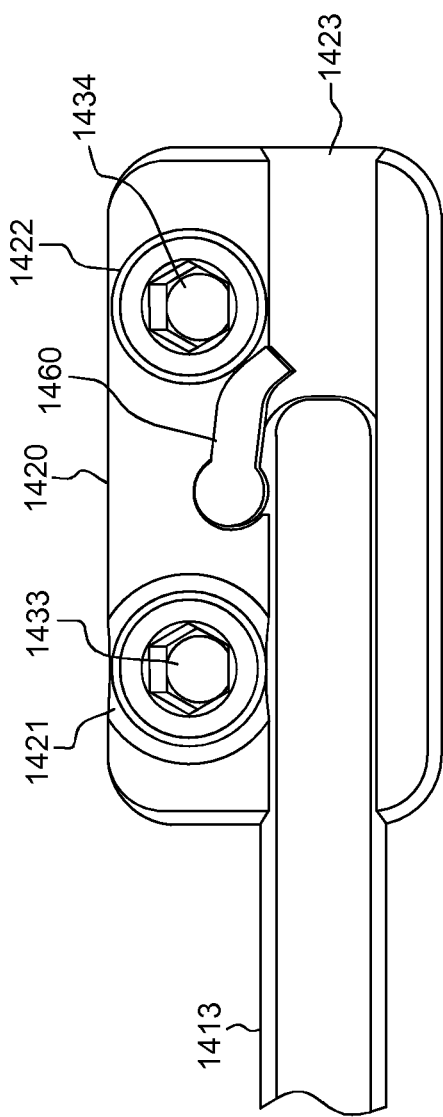
FIG. 14 illustrates an exemplary view of a ratcheting pawl to lock bone plate components in place, in accordance with an embodiment.

FIG. 14 illustrates an exemplary view of a ratcheting pawl to lock bone plate components in place, in accordance with an embodiment. FIG. 14 shows a male component 1413 and a second bone plate component 1420, in accordance with the embodiments of the present disclosure. In accordance with an embodiment, a ratcheting pawl may be used to lock male component 1413 in place after mating with female component 1423. Second bone plate component 1420 includes holes 1421 and 1422 for receiving bone screws 1433 and 1434, respectively. Second bone plate component 1420 further includes a female component 1423, which may be a receptacle for receiving male component 1413. A ratcheting pawl

1460, located on second bone plate component 1420, when unlocked, facilitates movement of male component 1413 within female component 1423. Ratcheting pawl 1460, as shown in FIG. 14 is locked, however, male component 1413 has not been inserted sufficiently to engage with ratcheting pawl 1460.

Figure 15:
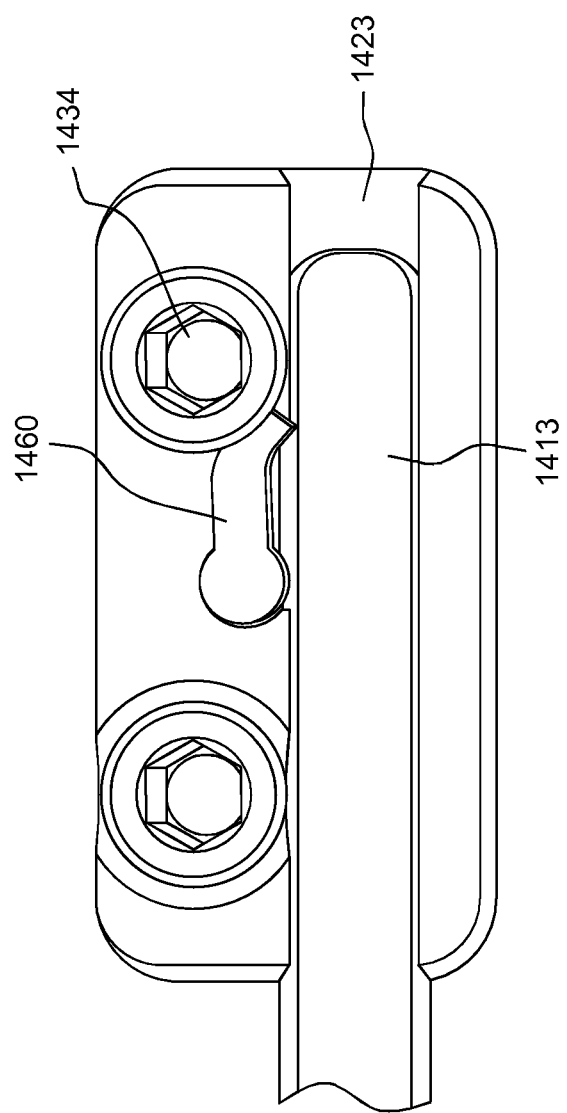
FIG. 15 illustrates an exemplary view of a ratcheting pawl to lock bone plate components in place, in accordance with an embodiment.

FIG. 15 illustrates an exemplary view of a ratcheting pawl to lock bone plate components in place, in accordance with an embodiment. FIG. 15 shows male member 1413 sufficiently inserted so as to engage with ratcheting pawl 1460, however, ratcheting pawl 1460 is in an unlocked position. Ratcheting pawl 1460 may be placed in a locked position based on a portion of a top end of bone screw 1434 contacting and impinging on the position of ratcheting pawl 1460, which would hold ratcheting pawl 1460 in place. When ratcheting pawl 1460 is held in place, it is in continuous contact with male component 1413, and thereby prevents male component 1414 from moving within female component 1423.

Figure 16:
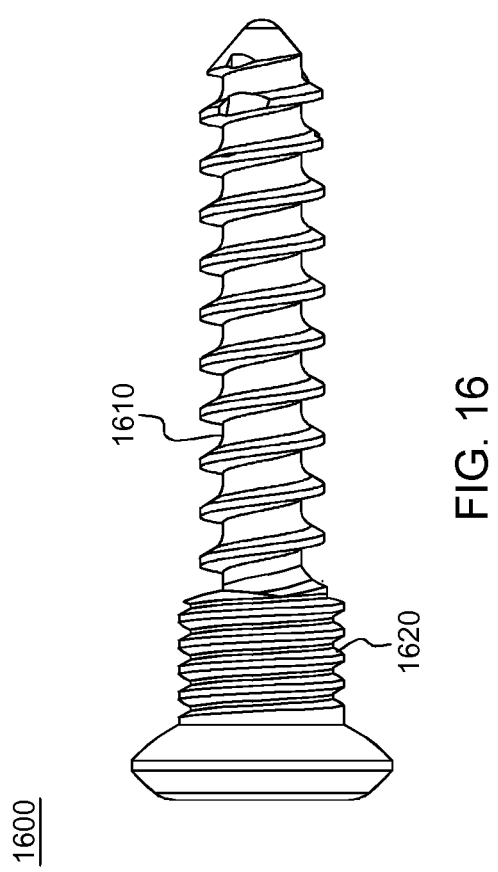
FIG. 16 illustrates an exemplary screw having both a bone and machine thread, in accordance with an embodiment.

FIG. 16 illustrates an exemplary screw having both a bone and machine thread, in accordance with an embodiment. FIG. 16 shows a bone screw 1600 which includes both bone and machine threads, for locking into both bone and into plate components. As shown, different threads, such as bone threads and machine threads, may have different thread pitches. Bone screw 1600 includes a section having bone threads 1610, and a section having machine threads 1620. Section 1610 including bone threads facilitates fixture and locking to bones. Section 1620 including machine threads facilitates fixture and locking into plate components. A bone screw with both machine and bone threads is advantageously able to lock both into a plate component through which it is screwed, as well as a bone in which it is inserted into, thus providing more secure fixture of a bone plate to a bone.

Figure 17:
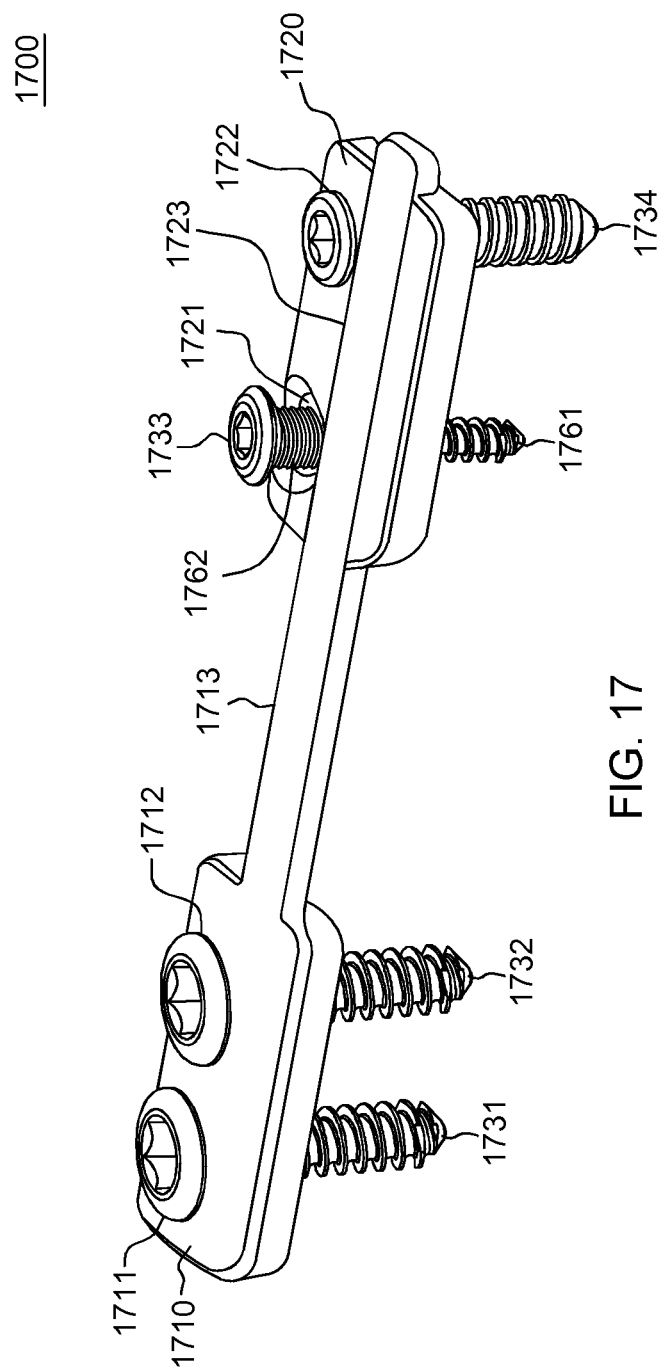
FIG. 17 illustrates an exemplary positioning of a dual threaded screw in a bone plate, in accordance with an embodiment.

FIG. 17 illustrates an exemplary positioning of a dual threaded screw in a bone plate, in accordance with an embodiment. FIG. 17 illustrates an implementation of a bone plate configured for receiving dual threaded screws in accordance with an embodiment of the present disclosure. Bone plate 1700, as shown, includes a first bone plate component 1710 and a second bone plate component 1720. First bone plate component 1710 includes holes 1711 and 1712 for receiving screws 1731 and 1732, respectively. Screws 1731 and 1732 are screwed into a first bone segment (not shown) through holes 1711 and 1712, respectively, to attach first bone plate component 1710 to the first bone segment. First bone plate component 1710 also includes a male component 1713 or dovetail, which is used for attaching first bone plate component 1710 to second bone plate component 1720 to facilitate compression of each of first bone plate component 1710 and second bone plate component 1720, which causes compression between the first bone segment and a second bone segment attached to second bone plate component 1720. The compression results in the creation of a corrective bone construct. Second bone plate component 1720 also includes holes, such as holes 1721 and 1722, for receiving screws 1733 and 1734, respectively. Bone screws 1733 and 1734 are screwed into a second bone segment (not shown) through holes 1721 and 1722, respectively, to attach second bone plate component 1720 to the second bone segment. Second bone plate component 1720 also includes a female component 1723, which may comprise a receptacle for receiving male component 1713.

After male component 1713 has been inserted into or mated with female component 1723, the position of male component 1713 within female component 1723 is adjustable, which results in an adjustment of the position of first bone plate component 1710 with respect to second bone plate component 1720. As each of first bone plate component 1710 and second bone plate component 1720 are attached to a corresponding bone segment, the position of the bone segments are also thus adjustable. Adjustment may result in compression of the bone segments, causing the bone segments to move closer to each other to form a corrective construct. Alternatively, it may result in stretching of the bone segments to provide for lengthening of the bone.

After adjustment of male component 1713 within female component 1723 is complete, the first bone plate component 1710 and the second bone plate component 1720 must be locked into place. Locking may be facilitated by numerous means. In an embodiment, a screw, such as those shown, may be tightened, resulting in the head of the screw impinging on the male component 1713, which results in locking the male component 1713 in place. As shown, for example, screw 1733 is a dual threaded screw which includes both bone threads and machine threads. A bone thread section represented by section 1761 is configured for attachment to bone. A machine thread section represented by section 1762 is configured for attachment to second plate component 1720 and configured for locking male component 1713 in place within female component 1723.

Figure 18:
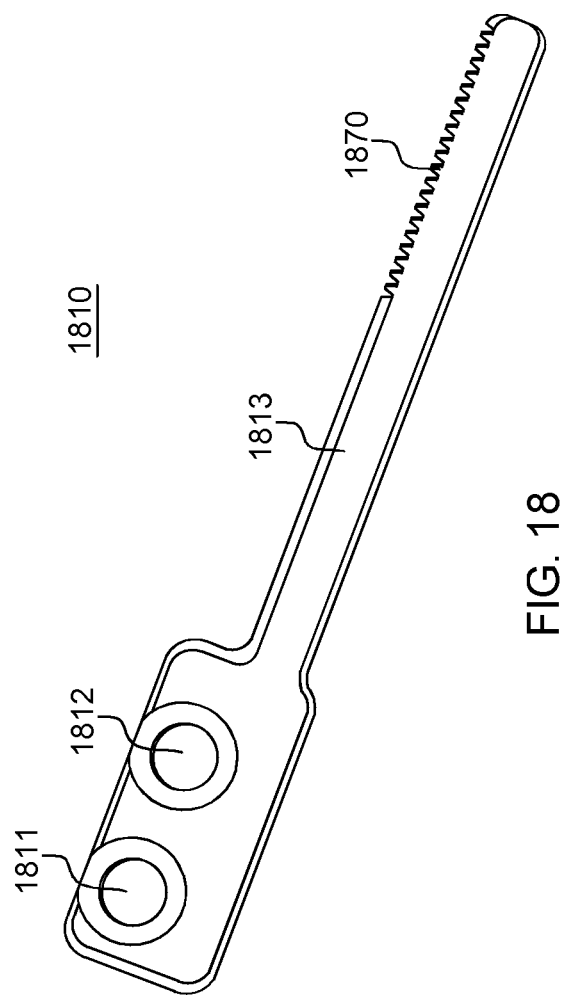
FIG. 18 illustrates a rack version of a component of a bone plate, in accordance with an embodiment.

FIG. 18 illustrates a rack version of a component of a bone plate, in accordance with an embodiment. FIG. 18 illustrates a first bone plate component 1810 of a bone plate in accordance with embodiments described by the present disclosure. First bone plate component 1810 is a rack version plate component, and includes holes 1811 and 1812 for receiving screws. First bone plate component 1810 also includes a male component 1813 for mating with a female component (not shown) to affix first bone plate component 1810 to a second bone plate component. Male component 1813 includes teeth or serrations 1870 adapted for engaging with a driver that can be used to adjust a position of male component 1813 with respect to a female component when male component 1813 and a female component are mated.

Figure 19:
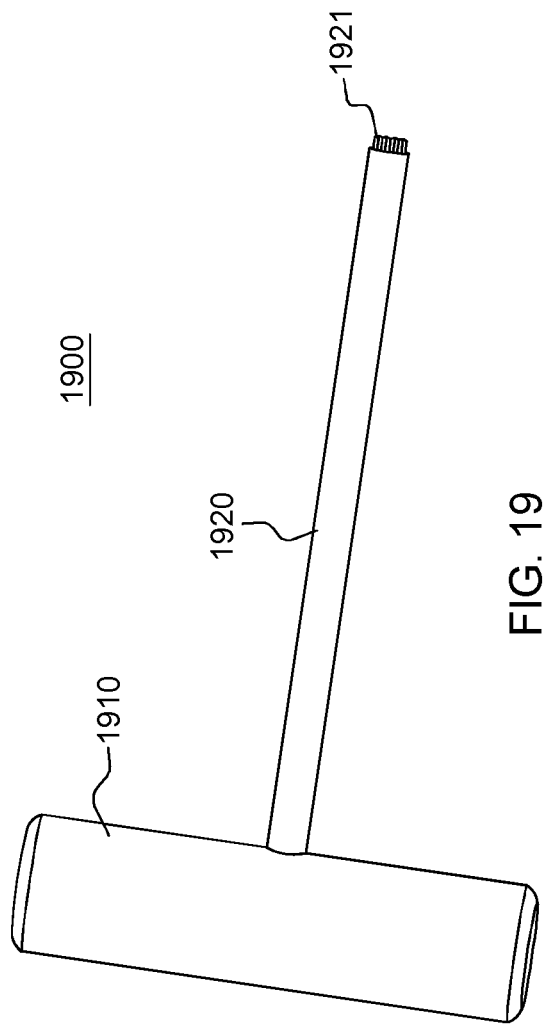
FIG. 19 illustrates an exemplary driver pinion used for affecting compression between components of a bone plate, in accordance with an embodiment.

FIG. 19 illustrates an exemplary driver pinion used for affecting compression between components of a bone plate, in accordance with an embodiment. FIG. 19 shows driver pinion 1900. Driver pinion 1900 includes a handle 1910, and an elongated member 1920, including a grooved or serrated end 1921. End 1921 is configured for engaging with teeth or serrations of a male component such as teeth 1870 of male component 1813. When end 1921 engages with the teeth, it causes the male component to move within a female component with which it is mated.

Figure 20:
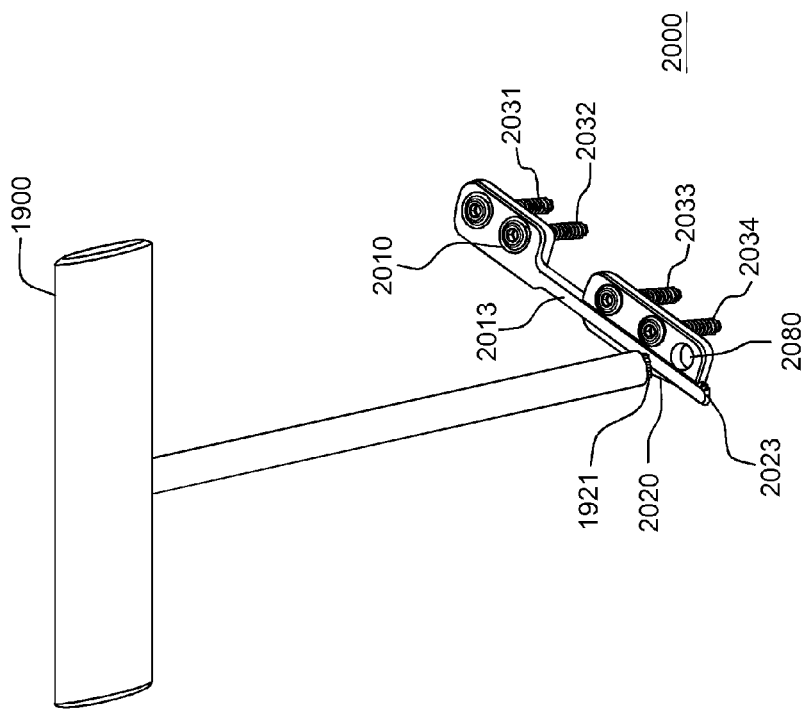
FIG. 20 illustrates an exemplary driver pinion and bone plate, in accordance with an embodiment.

FIG. 20 illustrates an exemplary driver pinion and bone plate, in accordance with an embodiment. FIG. 20 illustrates a driver pinion 1900 along with plate 2000, in accordance with the embodiments described by the present disclosure. Bone plate 2000, as shown, includes a first bone plate component 2010 and a second bone plate component 2020. First bone plate component 2010 includes holes for receiving bone screws 2031 and 2032, respectively. Bone screws 2031 and 2032 are screwed into a first bone segment (not shown) through their respective holes, respectively, to attach first bone plate component 2010 to the first bone segment. First bone plate component 2010 also includes a male component 2013 or dovetail, which is used for attaching first bone plate component 2010 to second bone plate component 2020 to facilitate compression of each of first bone plate component 2010 and second bone plate component 2020, which causes compression between the first bone segment and a second bone segment attached to second bone plate component 2020. The compression results in the creation of a corrective bone construct. Second bone plate component 2020 also includes holes for receiving screws 2033 and 2034, respectively. Screws 2033 and 2034 are screwed into a second bone segment (not shown) through their respective holes, to attach second bone plate component 2020 to the second bone segment. Second bone plate component 2020 also includes a female component 2023, which may comprise a receptacle for receiving male component 2013.

After male component 2013 has been inserted into or mated with female component 2023, the position of male component 2013 within female component 2023 is adjustable, which results in an adjustment of the position of first bone plate component 2010 with respect to second bone plate component 2020. As each of first bone plate component 2010 and second bone plate component 2020 are attached to a corresponding bone segment, the position of the bone segments are also thus adjustable. Adjustment may result in compression of the bone segments, causing the bone segments to move closer to each other to form a corrective construct.

Adjustment may be made using driver pinion 1900. End 1921 of driver pinion 1900 may be inserted into hole 2080 of second bone plate component 2020. After insertion of driver pinion 1900 into hole 2080, driver pinion 1900 may be turned, which causes end 1921 to engage with grooves or serrations of male component 2013. The engagement of end 1921 with the grooves or serrations will cause male component 2013 to move laterally within female component 2023 to which it is mated to. This results in an adjustment of position of male component 2013 within female component 2023.

After adjustment of male component 2013 within female component 2023 is complete, the first bone plate component 2010 and the second bone plate component 2020 must be locked into place. Locking may be facilitated by numerous means. In an embodiment, a bone screw, such as those shown, may be tightened, resulting in the head of the bone screw impinging on the male component 2013, which results in locking the male component 2013 in place.

Figure 21:
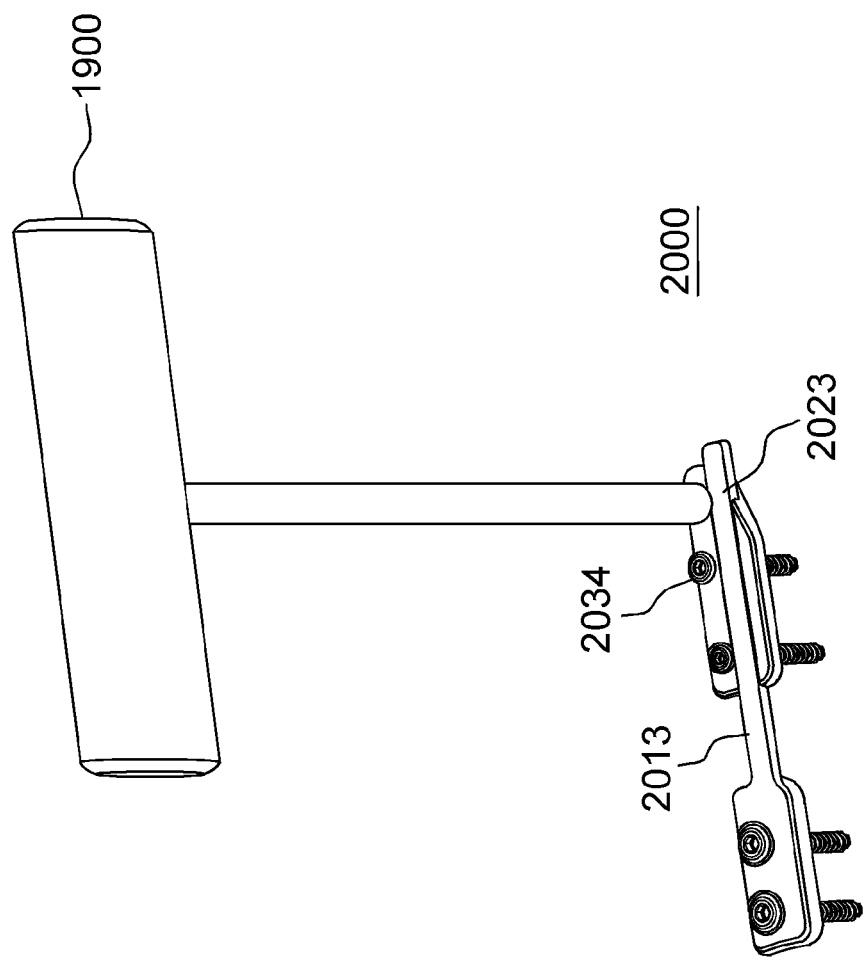
FIG. 21 illustrates an exemplary driver pinion and bone plate, in accordance with an embodiment.

FIG. 21 illustrates an exemplary driver pinion and bone plate, in accordance with an embodiment. FIG. 21 illustrates a different perspective view of driver pinion 1900 and bone plate 2000 as shown in FIG. 20. Driver pinion 1900 is inserted into hole 2080 to facilitate adjustment of a position of male component 2013 within female component 2023. Screw 2034 as shown is also in a raised position, thus facilitating the movement of male component 2013 within female component 2023.

Figure 22:
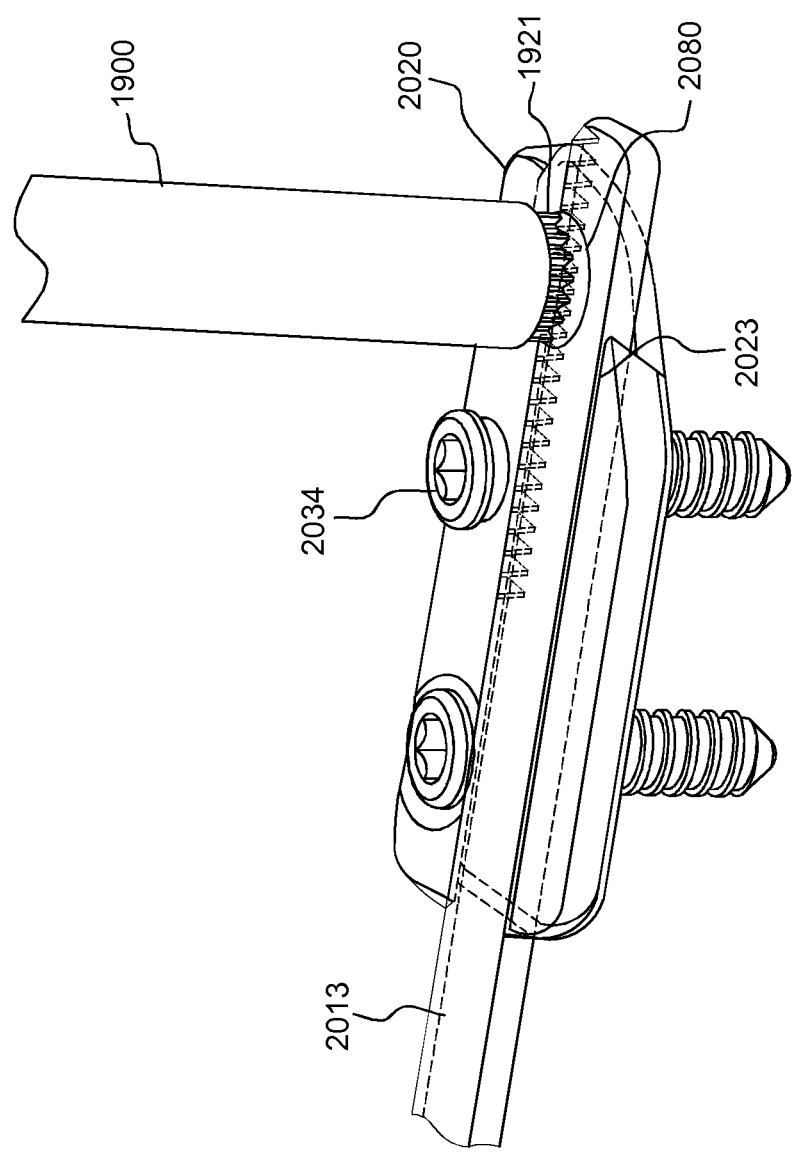
FIG. 22 illustrates a close up perspective view of a driver pinion used in a hole of a bone plate and causing compression, in accordance with an embodiment.

FIG. 22 illustrates a close up perspective view of a driver pinion used in a hole of a bone plate and causing compression, in accordance with an embodiment. FIG. 22 illustrates a close up perspective view of driver pinion 1900 inserted into hole 2080 of second bone plate component 2020. Male component 2013 as shown is mated with female component 2023. End 1921 of driver pinion 1900 is engaged with teeth or serrations of male component 2013. Turning driver pinion 1900 causes lateral movement of male component 2013 within female component 2023, which facilitates adjustment of the position of male component 2013. Once adjustment is complete, screw 2034 may be screwed into second bone plate component 2020 until screw 2034 contacts male component 2013, thereby locking male component 2013 into place.

Figure 23:
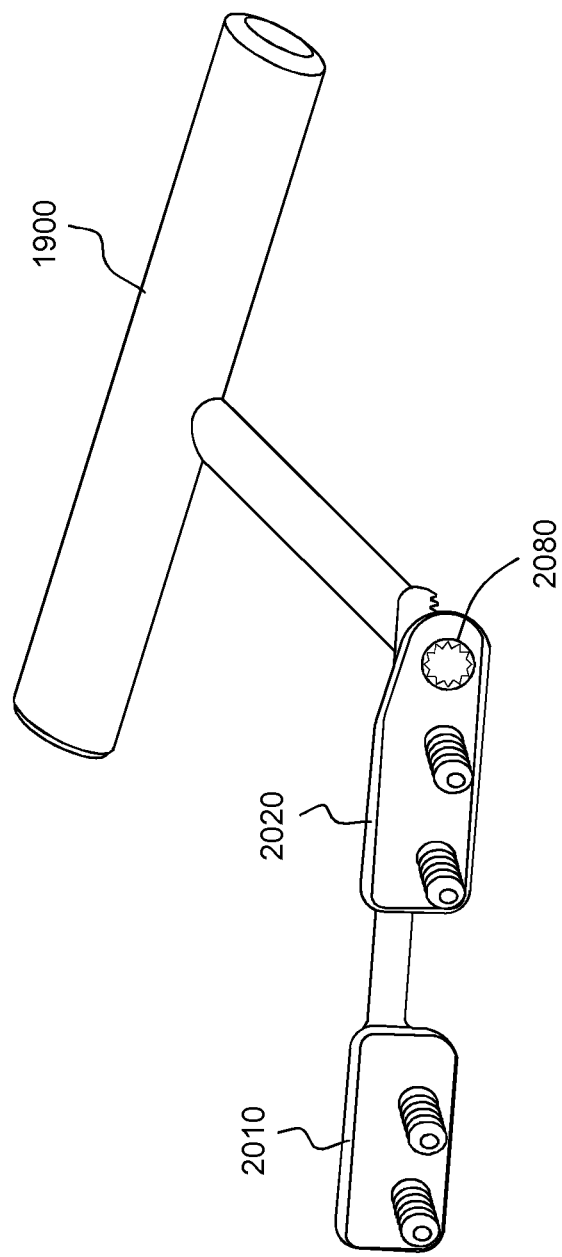
FIG. 23 illustrates a bottom view of a driver pinion used in a hole of a bone plate and causing compression, in accordance with an embodiment.

FIG. 23 illustrates a bottom view of a driver pinion used in a hole of a bone plate and causing compression, in accordance with an embodiment. FIG. 23 shows a bottom perspective view of driver pinion 1900 inserted into hole 2080 of second bone plate component 2020, as well as the entirety of bone plate 2000 from a bottom perspective after male component 2013 of first bone plate component 2010 is mated with the female component of second bone plate component 2020.

Figure 24:
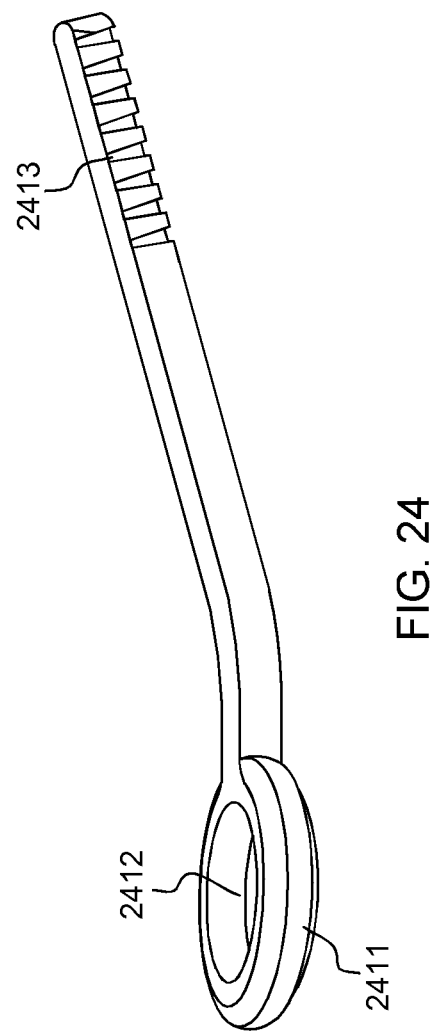
FIG. 24 illustrates a preformed bone plate component, in accordance with an embodiment.

FIG. 24 illustrates a preformed bone plate component, in accordance with an embodiment. FIG. 24 shows a male component 2410 which is a preformed male component for use with bone plates such as those shown in FIGS. 6-13 and described above in connection with these Figures. A first end 2411 of male component 2410 may be placed in a spherical bearing surface of a first plate component of a bone plate, in accordance with the embodiments described herein. Male component 2410 further includes a hole 2412 which is configured for receiving screws to affix male component 2410 to a first plate component, and thereby affix both the male component 2410 and first bone plate component to a first bone segment. Male component 2410 also includes grooves or serrations 2413 for engagement with a female component of a second bone plate component. As shown, male component 2410 is preformed, and thus, male component 2410 is formed at a predetermined angle to facilitate flexibility and precision in forming corrective constructs using a bone plate comprising a joined first bone plate component and a second bone plate component where male component 2410 facilitates the joining.

Figure 25:
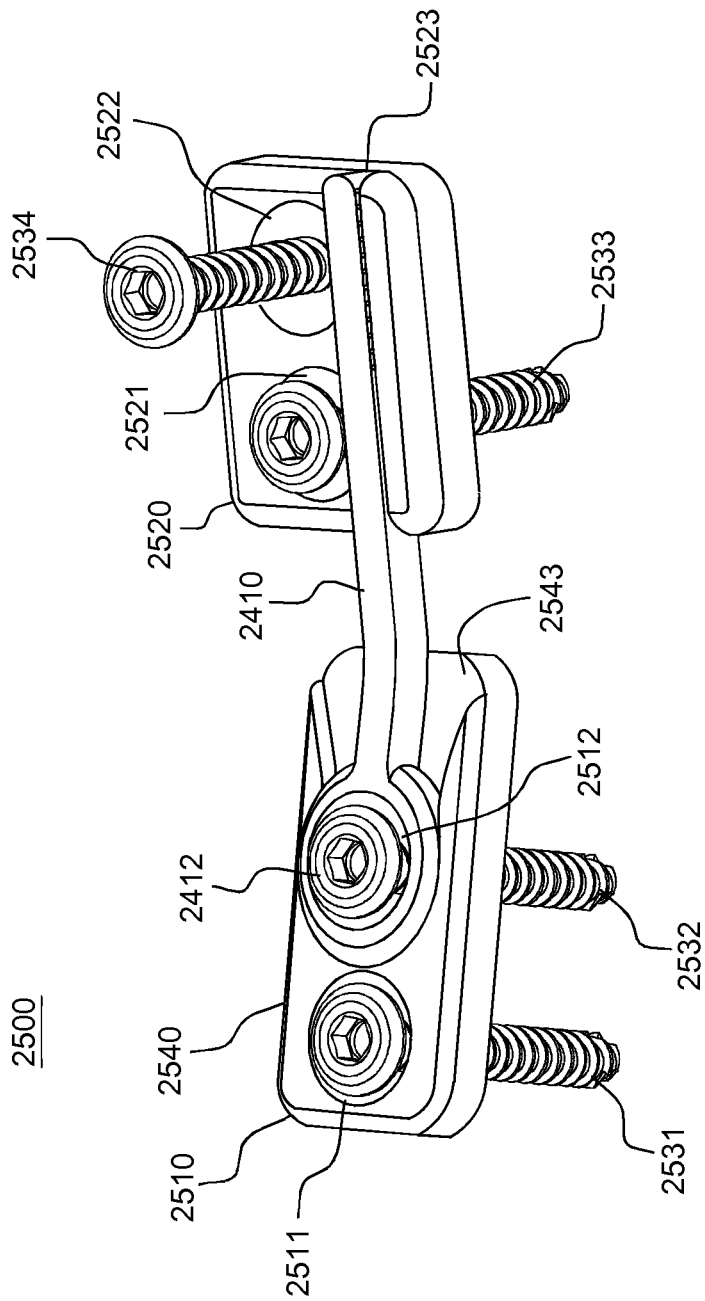
FIG. 25 illustrates an exemplary bone plate using a preformed bone plate component, in accordance with an embodiment.

FIG. 25 illustrates an exemplary bone plate using a preformed bone plate component, in accordance with an embodiment. Plate 25 shows bone plate 2500 including male component 2410 as shown and described with respect to FIG. 24. Bone plate 2500, as shown, includes a first bone plate component 2510 and a second bone plate component 2520. First bone plate component 2510 may include a base component 2540 which includes holes 2511 and 2512 for receiving bone screws 2531 and 2532, respectively. Bone screws 2531 and 2532 are screwed into a first bone segment (not shown) through holes 2511 and 2512, respectively, to attach first bone plate component 2510 to the first bone segment. First bone plate component 2510 also includes a male component 2410 which is used for attaching first bone plate component 2510 to second bone plate component 2520 to facilitate compression of each of first bone plate component 2510 and second bone plate component 2520, which causes compression between the first bone segment and a second bone segment attached to second bone plate component 2520. Male component 2410 may include a hole 2412 for receiving bone screw 2532 that goes through both hole 2412 and hole 2512 to hold lock male component 2410 to base component 2540 of first bone plate component 2510. Base component 2540 further includes a bearing surface 2543 which facilitates multiplanar movement of male component 2410, allowing for angular adjustments to be made to male component 2410. The compression results in the creation of a corrective bone construct. A spherical bearing surface facilitates reduction of complex fractures or closure of segments without geometric surfaces or pathways.

In an embodiment, male component 2410 is placed into the bearing surface 2543 of base component 2540. Once a multiplanar angle of male component 2410 has been selected, a bone screw 2532 may be inserted through both hole 2512 and hole 2412. Once bone screw 2532 is tightened or fastened, male component 2410 is locked into place in bearing surface 2543 with respect to base component 2540.

Second bone plate component 2520 also includes holes, such as holes 2521 and 2522, for receiving screws 2533 and 2534, respectively. Bone screws 2533 and 2534 are screwed into a second bone segment (not shown) through holes 2521 and 2522, respectively, to attach second bone plate component 2520 to the second bone segment. Second bone plate component 2520 also includes a female component 2523, which may comprise a receptacle for receiving a male component such as male component 2410.

Either or both male component 2410 or female component 2523 may include serrations or grooves to increase resistance, thus providing a more secure locking mechanism and also allowing for more precise adjustments. For example, male component 2410 includes teeth or serrations 2413 cut along a portion of its bottom surface. This allows male component 2410 to function as a gear rack. Thus, an external pinion gear (not shown) may engage the teeth or serrations to provide bone compression, distraction, or both. Turning or usage of the pinion gear will cause adjustment of a position of the male component 2410 in either of two directions laterally with respect to female component 2523. This in turn results in adjustments of position between first bone plate component 2510 and second bone plate component 2520.

In an embodiment, male component 2410 is locked into place within female component 2523 based on a tightening of bone screws 2533 and/or 2534. As shown in FIG. 25, bone screws 2533 and 2534, when tightened, press against male component 2410, thereby preventing male component 2410 from moving within female component 2523.

Figure 26:
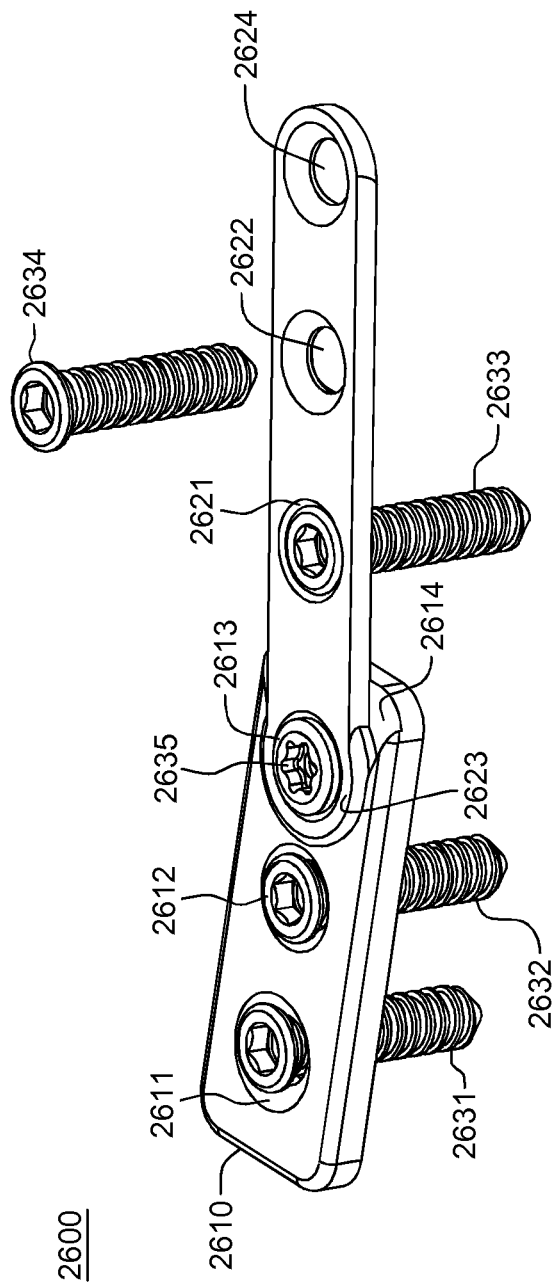
FIG. 26 illustrates an exemplary bone plate, in accordance with an embodiment.

FIG. 26 illustrates an exemplary bone plate, in accordance with an embodiment. FIG. 26 shows bone plate 2600 which comprises a first bone plate component 2610 and a second bone plate component 2620. First bone plate component 2610 comprises holes 2611 and 2612 for receiving bone screws 2631 and 2632 facilitating attachment of first bone plate component 2610 to a first bone segment (not shown). First bone plate component 2610 also includes hole 2613 which facilitates attachment of second bone plate component 2620 to first bone plate component 2610. A spherical bearing surface 2614 of first bone plate component 2610 is configured to receive a first end of second bone plate component 2620. Second bone plate component 2620 may be adjusted in a multiplanar direction in spherical bearing surface 2614. The first end of second bone plate component 2620 may comprise a hole 2623, which receives screw 2635. Screw 2635 may be inserted through both hole 2623 and hole 2613 in order to lock second bone plate component 2620 to first bone plate component 2610 after any necessary adjustments are made to the multiplanar position of second bone plate component 2620. As screw 2635 in this embodiment is used for securement purposes, screw 2635 may be machine threaded.

Second bone plate component 2620 may further comprise holes 2621, 2622, and 2624, for receiving bone screws such as bone screws 2633 and 2634. Bone screws are inserted through holes 2621, 2622, and 2624 to attach second bone plate component 2620 to a second bone segment (not shown).

After each of the first bone plate component 2610 and the second bone plate component 2620 are affixed to their respective first bone segment and second bone segment, a first end of second bone plate component 2620 may be received by spherical bearing surface 2614. Second bone plate component 2620 may then receive a multiplanar adjustment. Once a final adjustment position is reached, screw 2635 is inserted through hole 2623 and hole 2613 to lock second bone plate component 2620 in place with respect to first bone plate component 2610.

Figure 27:
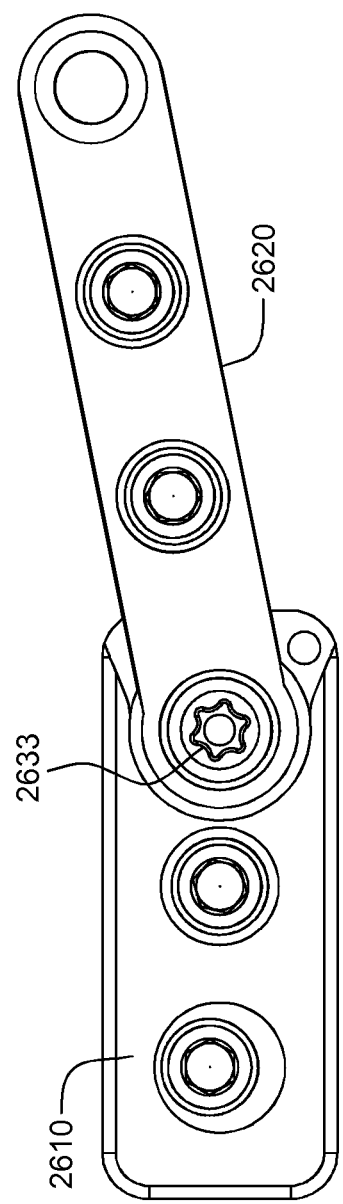
FIG. 27 illustrates a top view of an exemplary bone plate, in accordance with an embodiment.

FIG. 27 illustrates a top view of an exemplary bone plate, in accordance with an embodiment. FIG. 27 illustrates a top view of bone plate 2600 as also shown in FIG. 26. Second bone plate component 2620, as shown, has been adjusted to an angle with respect to first bone plate component 2610. Second bone plate component 2620 is locked in position with respect to first bone plate component 2610 by screw 2633.

Figure 28:
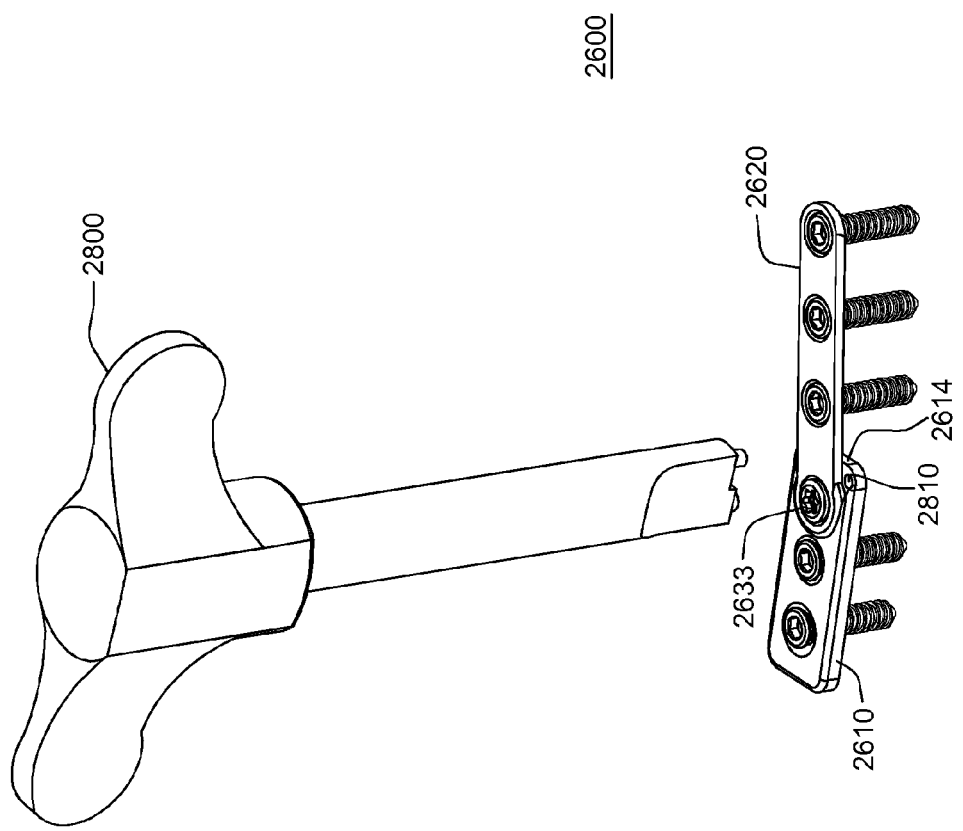
FIG. 28 illustrates a two pin external tool used for articulating a bone plate, in accordance with an embodiment.

FIG. 28 illustrates a two pin external tool used for articulating a bone plate, in accordance with an embodiment. FIG. 28 illustrates bone plate 2600 and a two pin external tool 2800 for articulating the first bone plate component 2610 and the second bone plate component 2620 of bone plate 2600. Two pin external tool 2800 comprises two pins, which engage with screw 2633 and a hole 2810 of first bone plate component 2610 located on spherical bearing surface 2614.

Figure 29:
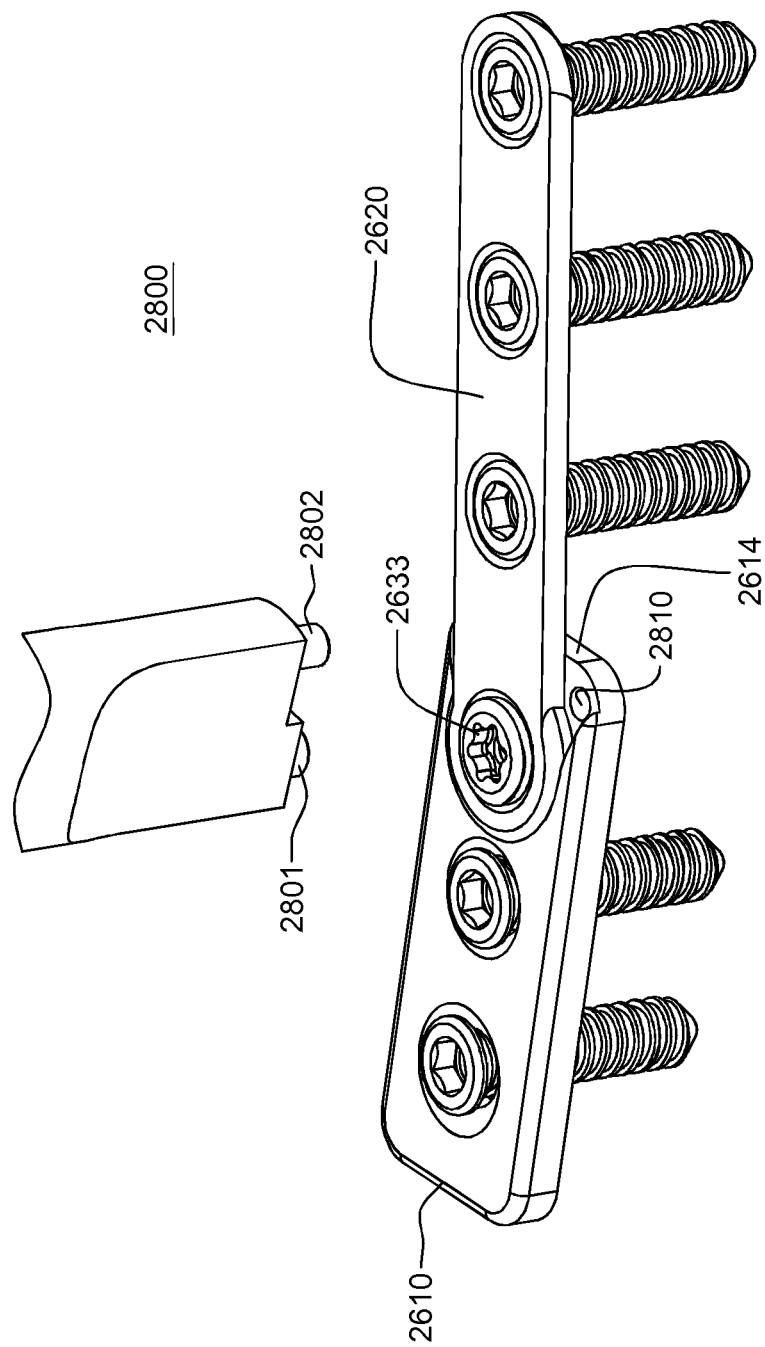
FIG. 29 illustrates a close up view of a two pin external tool with bone plate, in accordance with an embodiment.

FIG. 29 illustrates a two pin external tool used for articulating a bone plate, in accordance with an embodiment. FIG. 29 illustrates a close up view of the section of bone plate 2600 which engages with two pin external tool 2800. Pin 2801 of two pin external tool 2800 is configured to engage with screw 2633. Pin 2802 of two pin external tool 2800 is configured to engage with hole 2810 of first bone plate component 2610 located on spherical bearing surface 2614. When pins 2801 and 2802 are engaged, the position and/or angle of second bone plate component 2620 can be adjusted with respect to first bone plate component 2610.

Figure 30:
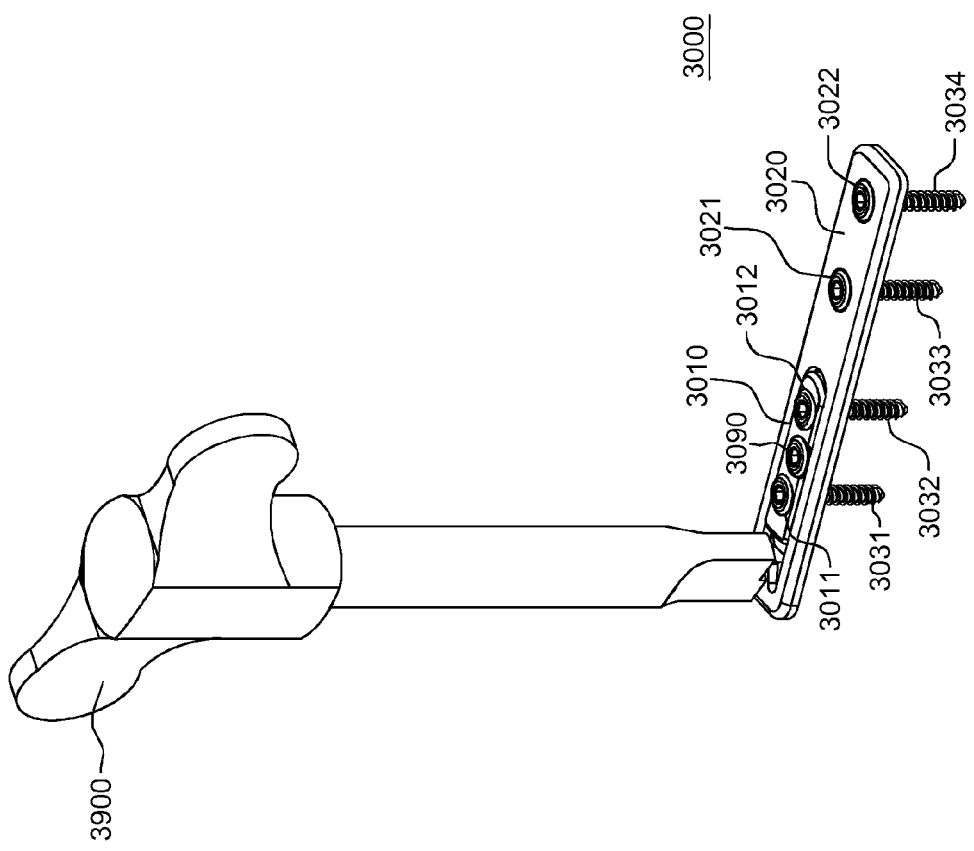
FIG. 30 illustrates an exemplary driver with bone plate, in accordance with an embodiment.

FIG. 30 illustrates an exemplary driver with bone plate, in accordance with an embodiment. FIG. 30 illustrates a two pin external tool or driver 3900 and a bone plate 3000. Bone plate 3000, as shown, includes a first bone plate component 3010 and a second bone plate component 3020. First bone plate component 3010 includes holes 3011 and 3012 for receiving bone screws 3031 and 3032, respectively. Bone screws 3031 and 3032 are screwed into a first bone segment (not shown) through holes 3011 and 3012, respectively, to attach first bone plate component 3010 to the first bone segment. First bone plate component 3010 represents or may include a male component and may mate with second bone plate component 3020 to facilitate compression of each of first bone plate component 3010 and second bone plate component 3020, which causes compression between the first bone segment and a second bone segment attached to second bone plate component 3020. The compression results in the creation of a corrective bone construct. Second bone plate component 3020 also includes holes, such as holes 3021 and 3022, for receiving screws 3033 and 3034, respectively. Bone screws 3033 and 3034 are screwed into a second bone segment (not shown) through holes 3021 and 3022, respectively, to attach second bone plate component 3020 to the second bone segment. Second bone plate component 3020 may also represent or include a female component which means that second bone plate component 3020 may serve as a receptacle for receiving first bone plate component 3010.

After first bone plate component 3010 has been inserted into a receptacle of second bone plate component 3020, the position of first bone plate component 3010 within second bone plate component 3020 is adjustable. As each of first bone plate component 3010 and second bone plate component 3020 are attached to a corresponding bone segment, the position of the bone segments are also thus adjustable. Adjustment may result in compression of the bone segments, causing the bone segments to move closer to each other to form a corrective construct.

After adjustment of first bone component 3010 within second bone component 3020 is complete, the first bone plate component 3010 and the second bone plate component 3020 must be locked into place. Locking may be facilitated by numerous means. In an embodiment, a screw, such as screw 3090, may be tightened, resulting in the head of the bone screw impinging on the surface of both first bone plate component 3010 and second bone plate component 3020, which results in locking the first bone plate component 3010 in place.

Figure 31:
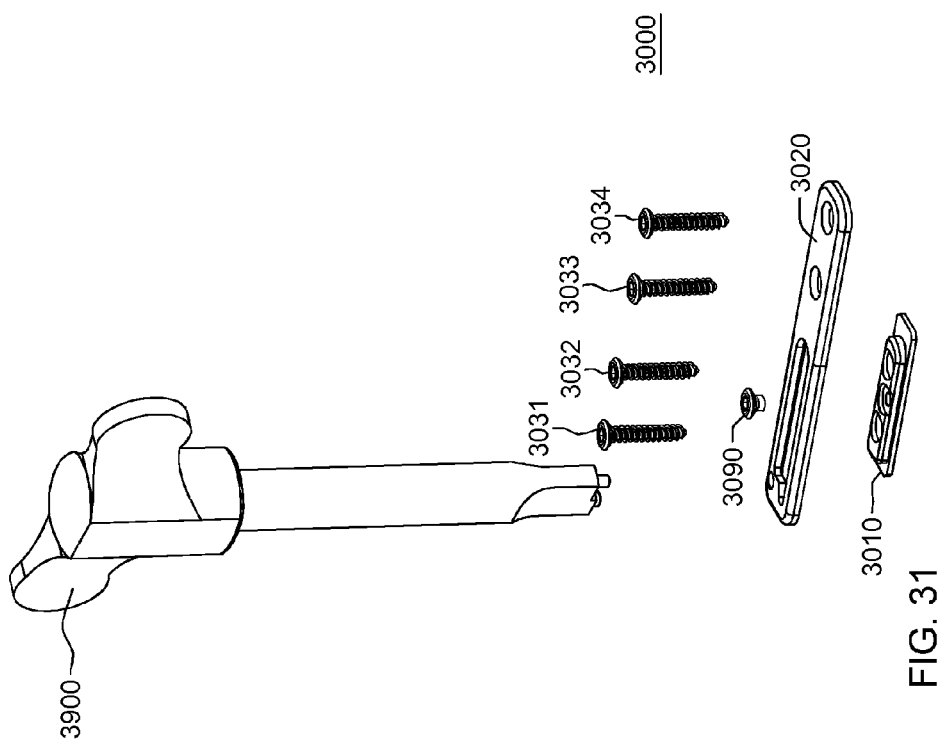
FIG. 31 illustrates an exemplary driver with bone plate, in accordance with an embodiment.

FIG. 31 illustrates an exemplary driver with bone plate, in accordance with an embodiment. FIG. 31 illustrates bone plate 3000 and two pin external tool 3900, with all components of bone plate 3000 unattached. As shown, first plate component 3010 is disengaged from a receptacle of second bone plate component 3020. Bone screws 3031, 3032, 3033, and 3034 are shown. Screw 3090 which may include machine threads is shown. Screw 3090 is not a bone screw as its purpose is to hold the position of first bone plate component 3010 within second bone plate component 3020.

Figure 32:
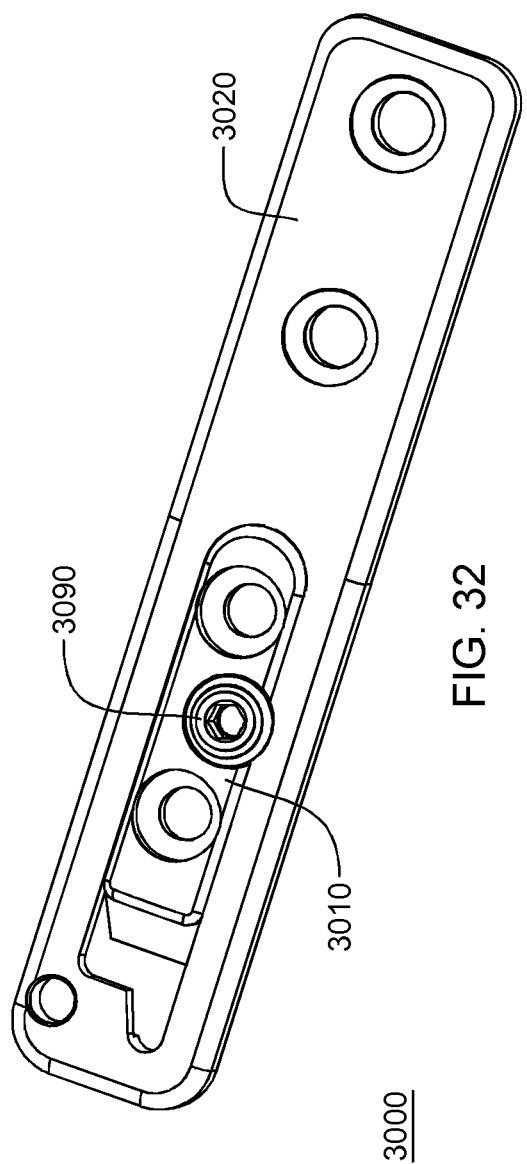
FIG. 32 illustrates an exemplary bone plate, in accordance with an embodiment.

FIG. 32 illustrates an exemplary bone plate, in accordance with an embodiment. FIG. 32 illustrates bone plate 3000 with first bone plate component 3010 and second bone plate component 3020 locked into position by screw 3090.

Figure 33:
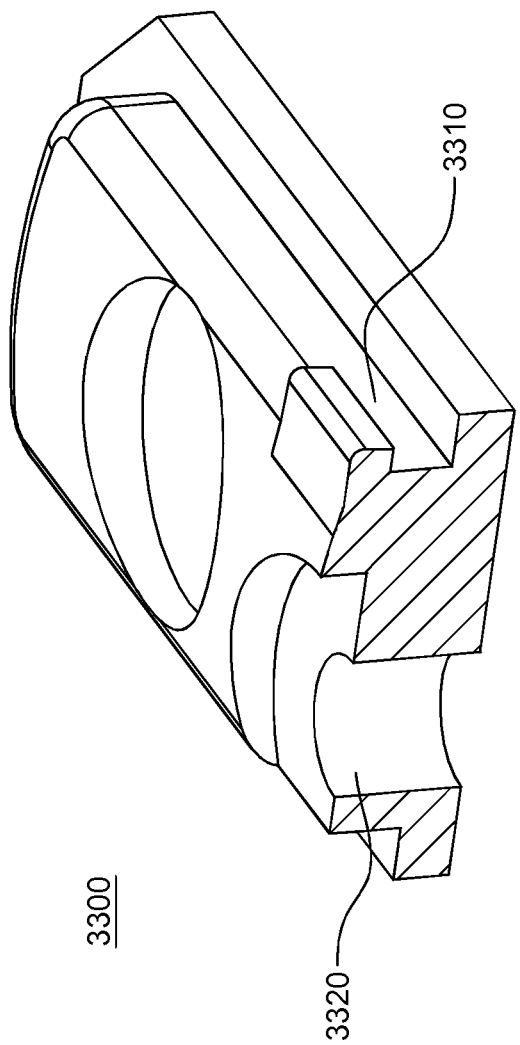
FIG. 33 illustrates a retained slider of a component of a bone plate, in accordance with an embodiment.

FIG. 33 illustrates a retained slider of a component of a bone plate, in accordance with an embodiment. FIG. 33 illustrates a close up view of an exemplary male component 3300 which comprises a single side retained slider for mating with a female component. Male component 3300 includes retained slider 3310 which may slide within a track provided by a female component. Male component 3300 relies on a screw for retention as shown by hole 3320 which receives the screw.

Figure 34:
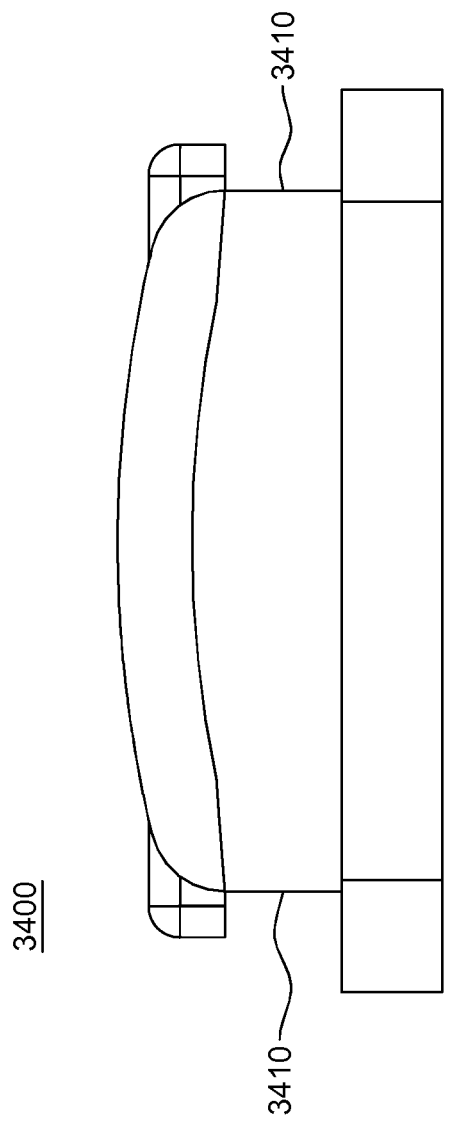
FIG. 34 illustrates a dual sided snap fit sliding component of a bone plate, in accordance with an embodiment.

FIG. 34 illustrates a dual sided snap fit sliding component of a bone plate, in accordance with an embodiment. FIG. 34 illustrates a frontal view of a male component 3400, which includes two snap fit sliding components 3410, which facilitates male component 3400 being placed within a female component by a snapping means which locks male component 3400 within a track of the female component to move within the track.

Figure 35:
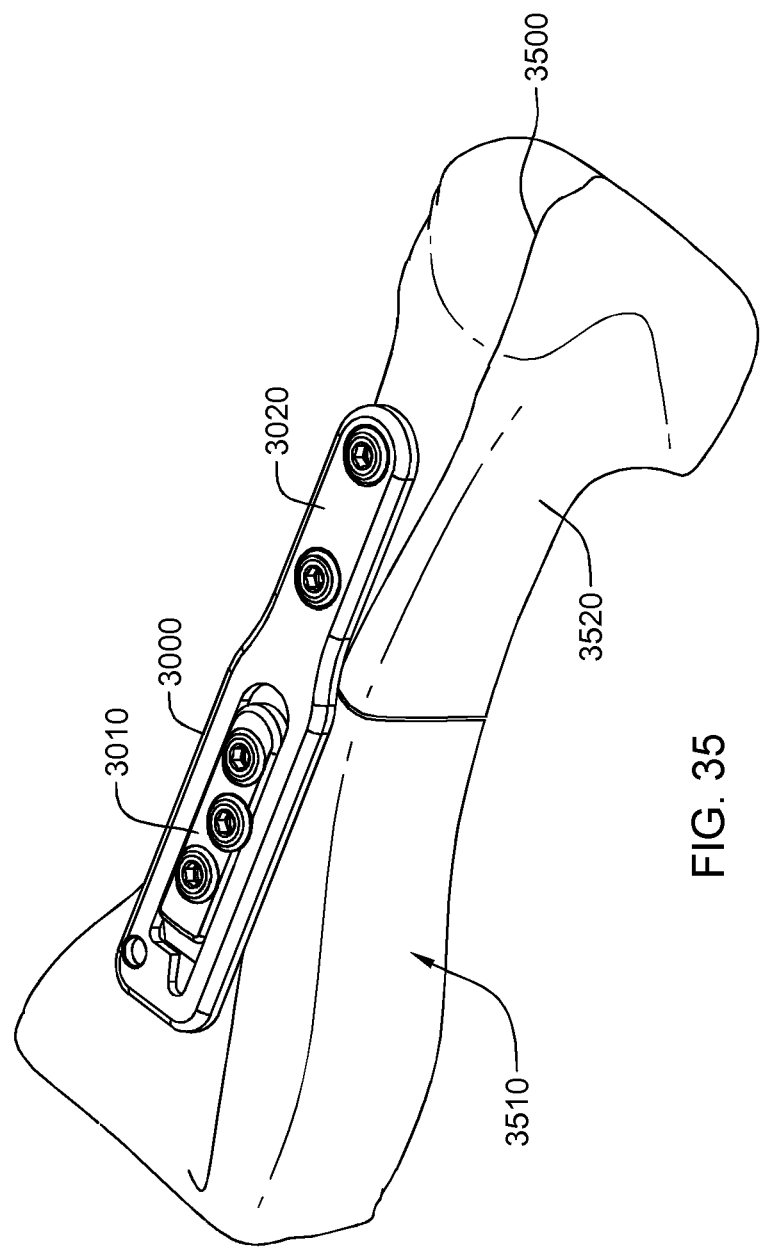
FIG. 35 illustrates an exemplary bone plate implanted in a bone, in accordance with an embodiment.

FIG. 35 illustrates an exemplary bone plate implanted in a bone, in accordance with an embodiment. FIG. 35 shows exemplary bone plate 3000 implanted in a bone 3500. As shown, first bone plate component 3010 is affixed to a first bone segment 3510 and second bone plate component 3020 is affixed to a second bone segment 3520.

Furthermore, any of the embodiments described herein are not meant to be limiting and any combination of features of the embodiments described herein that could or would be implemented by one of ordinary skill in the art should be recognized.

The foregoing Detailed Description is understood as being in every respect illustrative and exemplary, but not restrictive, and the scope of the embodiments disclosed herein is not to be determined from the Detailed Description, but rather from the claims as interpreted according to the full breadth permitted by the patent laws. It is understood that the embodiments shown and described herein are only illustrative of the principles of the present invention and that various modifications may be implemented by those skilled in the art without departing from the scope and spirit of the disclosure. Those skilled in the art could implement various other feature combinations without departing from the scope and spirit of the disclosure.

We claim:

1. A dynamic bone plate, comprising:
   a first bone plate component, comprising:
      at least one hole configured for receiving bone screws for attachment to a first bone segment; and
      a male component;
   a second bone plate component, comprising:
      at least one hole configured for receiving bone screws for attachment to a second bone segment; and
      a female component configured for mating with the male component of the first bone plate component;
      wherein a portion of at least one of the at least one holes in the second bone plate extends into a side portion of the female component;
   wherein the male component is adjustable after mating with the female component to adjust a position of the first bone plate component with respect to the second bone plate component and wherein the male component is locked into place with respect to the female component by at least one bone screw inserted through the at least one hole of the second bone plate component causing compression between the first bone segment and the second bone segment to form a corrective construct.

2. The dynamic bone plate of claim 1, wherein the male component comprises an elongated member receivable by the female component in a dovetail configuration.

3. The dynamic bone plate of claim 1, wherein the female component comprises a dovetail receptacle configured for receiving the male component in a dovetail configuration.

4. The dynamic bone plate of claim 1, wherein the male component and the female component, when mated, fit telescopically.

5. The dynamic bone plate of claim 1, wherein tightening of a bone screw inserted through a hole of the at least one hole of the second bone plate component, causes a head of the bone screw to impinge on one edge of the male component mated with the female component and lock the male component in place within the female component.

6. The dynamic bone plate of claim 1, wherein tightening of a secondary locking bone screw inserted through a hole of the at least one hole of the second bone plate component, causes the male component to lock into place within the female component by interference.

7. The dynamic bone plate of claim 6, wherein when the secondary locking bone screw is not fully screwed through the hole, the male component is capable of sliding within the female component.

8. The dynamic bone plate of claim 1, wherein the bone screws each comprise at least one thread.

9. The dynamic bone plate of claim 1, wherein the bone screws are each dual thread screws.

10. The dynamic bone plate of claim 9, wherein the dual thread screws each comprise a bone thread and a machine thread, wherein the bone thread is configured for attaching to bone, and the machine thread is configured for attaching to portions of the dynamic bone plate.

11. The dynamic bone plate of claim 1, wherein the bone screws are screwed through the at least one holes using an external tool.

12. A dynamic plate, comprising:
    a first plate component, comprising:
       at least one hole configured for receiving screws for attachment to a first body segment; and
       a male component;
    a second plate component, comprising:
       at least one hole configured for receiving screws for attachment to a second body segment; and
       a female component configured for mating with the male component of the first plate component;
       wherein the at least one hole of the second plate component overlaps with a side portion of the female component;
    wherein the male component is adjustable after mating with the female component to adjust a position of the first plate component with respect to the second plate component and wherein the male component is locked into place with respect to the female component by at least one screw inserted through the at least one hole of the second plate component causing compression between the first body segment and the second body segment to form a corrective construct.

13. The dynamic plate of claim 12, wherein the male component comprises an elongated member receivable by the female component in a dovetail configuration.

14. The dynamic plate of claim 12, wherein the female component comprises a dovetail receptacle configured for receiving the male component in a dovetail configuration.

15. The dynamic plate of claim 12, wherein the male component and the female component, when mated, fit telescopically.

16. The dynamic plate of claim 12, wherein tightening of a screw inserted through a hole of the at least one hole of the second plate component, causes a head of the screw to impinge on a side of the male component mated with the female component and lock the male component in place within the female component.

17. The dynamic plate of claim 12, wherein tightening of a secondary locking screw inserted through a hole of the at least one hole of the second plate component, causes the male component to lock into place within the female component by interference.

18. The dynamic plate of claim 17, wherein when the secondary locking bone screw is not fully screwed through the hole, the male component is capable of sliding within the female component.

19. The dynamic plate of claim 12, wherein the screws each comprise at least one thread.

20. The dynamic plate of claim 12, wherein the screws are each dual thread screws.

21. The dynamic plate of claim 12, wherein the screws are screwed through the at least one holes using an external tool.

\* \* \* \* \*